US007785783B2

(12) United States Patent
Morley et al.

(10) Patent No.: US 7,785,783 B2
(45) Date of Patent: Aug. 31, 2010

(54) METHOD OF ANALYSING A MARKER NUCLEIC ACID MOLECULE

(75) Inventors: Alexander Alan Morley, Glenelg (AU); Michael Brisco, Campbelltown (AU); Pamela Sykes, Bellevue Heights (AU)

(73) Assignee: Monoquant Pty Ltd., Adelaide, South Australia (AU)

( * ) Notice: Subject to any disclaimer, the term of this patent is extended or adjusted under 35 U.S.C. 154(b) by 213 days.

(21) Appl. No.: 10/844,603

(22) Filed: May 13, 2004

(65) Prior Publication Data

US 2005/0255482 A1    Nov. 17, 2005

(30) Foreign Application Priority Data

May 13, 2003    (AU) .............................. 2003902299

(51) Int. Cl.
 *C12Q 1/68*    (2006.01)
(52) U.S. Cl. ........................................................... 435/6
(58) Field of Classification Search ........................ None
 See application file for complete search history.

(56) References Cited

U.S. PATENT DOCUMENTS

2002/0106665 A1*    8/2002    Southern et al. ............... 435/6

FOREIGN PATENT DOCUMENTS

WO    WO/01/79534    10/2001

OTHER PUBLICATIONS

Szczepek et al, Blood 92 (8), 2844 (1998).*
International Search Report dated Aug. 17, 2004, directed at counterpart international application No. PCT/AU2004/000625.
Assaf et al. (2000). "High detection rate of T-cell receptor beta chain rearrangements in T-cell lymphoproliferations by family specific polymerase chain reaction in combination with the GeneScan technique and DNA sequencing," *Blood* 96(2): 640-646.
Beers et al. (1993). "Ex vivo clonotype primer-directed gene amplification to identify malignant T cell repertoires," *Journal of Leukocyte Biology* 54: 343-350.
Ma et al. (2000). "Multiplex Polymerase Chain Reaction-Based Analysis of T-Cell Receptor Y Gene Rearrangements for the Determination of T-Lymphocyte Clonality," *Environmental and Molecular Mutagenesis* 35:1-8.
Szczepanski et al. (1999). "Cross-lineage T cell receptor gene rearrangements occur in more than ninety percent of childhood precursor-B acute lymphoblastic leukemias: alternative PCR targets for detection of minimal residual disease," *Leukemia* 13:196-205.
Van Dongen et al. (2003). "Design and standardization of PCR primers and protocols for detection of clonal immunoglobulin and T-cell receptor gene recombinations in suspect lymphoproliferations: Report of the BIOMED-2 Concerted Action BMH4-CT98-3936," *Leukemia* 17:2257-2317.
Zemlin et al. (1998). "Improved Polymerase Chain Reaction Detection of Clonally Rearranged T-Cell Receptor β Chain Genes,"*Diagn Mol Pathol* 7(3): 138-145.

Fliss et al. (Mar. 17, 2000). "Facile Detection of Mitochondrial DNA Mutations in Tumors and Bodily Fluids," *Science* 287:2017-2019.
Strong et al. (Jan. 1985). "Human Acute Leukemia Cell Line With the t (4;11) Chromosomal Rearrangement Exhibits B Lineage and Monocytic Characteristics," *Blood* 65(1):21-31.
Trakhtenbrot et al. (1995). "Hexasomy of Chromosome 8 and Trisomy of Chromosome 11 Characterize Two Karyotypically Independent Clones in a Case of Acute Non-lymphocytic Leukemia," *Cancer Genet Cytogenet* 85:1-4.
Miyazaki et al. (2001). "Flow cytometric analysis of hemetopoietic progenitor cells in peripheral blood stem cell harvest from patients with CD34 positive acute leukemia," *Journal of Immunological Methods* 247:9-15.
Stinear et al. (Apr. 1999). "Identification and Characterization of IS2404 and IS2606: Two Distinct Repeated Sequences for Detection of *Mycobacterium ulcerans* by PCR," *Journal of Clinical Microbiology* 37(4):1018-1023.
Yates and Holmes. (May 1987). "Two Families of Repeated DNA Sequences in *Thiobacillus ferrooxidans*," *Journal of Bacteriology* 169(5):1861-1870.
Pearson and Morrow. (Jul. 1981). "Discrete-length repeated sequences in eukaryotic genomes," *Proc. Natl. Acad. Sci.* 78(7):4016-4020.
Tutter and Riblet. (Oct. 1989). "Conservation of an immunoglobulin variable-region gene family indicates a specific, noncoding function," *Proc. Natl. Acad. Sci.* 86:7460-7464.
Borghesi-Nicoletti and Schulze. (1991). "Polymerase Chain Reaction of Genes Flanked by Short Noncontiguous Sequence Motifs," *Analytical Biochemistry* 192:449-452.
Guglielmi et al. (Aug. 1988). "Use of a variable α region to create a functional T-cell receptor δ chain," *Proc. Natl. Acad. Sci.* 85:5634-5638.
Gestri et al. (2001). "Oligoclonal T cell repertoire in cerebrospinal fluid of patients with inflammatory diseases of the nervous system," *J. Neurol Neurosurg. Psychiatry* 70:767-772.
Struyk et al. (1994). "Evidence for selective in vivo expansion of synovial tissue-infiltrating CD4 $^+$CD45RO$^+$ T lymphocytes on the basis of CDR3 diversity," *International Immunology* 6(6):897-907.

(Continued)

*Primary Examiner*—James Martinell
(74) *Attorney, Agent, or Firm*—Morrison & Foerster LLP

(57) ABSTRACT

The present invention relates to a method of characterizing a nucleic acid region and, more particularly, to a method of analysing a marker nucleic acid region. The method of the present invention is based on identification of one or both of the nucleic acid regions flanking a marker nucleic acid region and provides a means of analysing a marker nucleic acid region which is characteristic of a clonal population of cells. The method of the present invention is useful in the context of enabling a range of applications including, but not limited to, monitoring the progression of a condition characterized by the presence of a clonal populations of cells (such as a neoplastic condition), monitoring the levels of one or more clonal cell population, predicting the likelihood of a subject's relapse from a remissive state to a disease state, for assessing the effectiveness of existing therapeutic drugs and/or new therapeutic agents and identifying the presence of a marker region.

36 Claims, 1 Drawing Sheet

OTHER PUBLICATIONS

Rettig et al. (Apr. 1, 1996). "$V_H$ Gene Usage in Multiple Myeloma: complete Absence of the $V_H4.21$ ($V_H4-34$) Gene," *Blood* 87(7):2846-2852.

Pritsch et al. (1999). "$V_H$ gene usage by family members affected with chronic lymphocytic leukaemia," *British Journal of Haematology* 107:616-624.

Sartono et al. (1997). "Selective usage of defined TCRBV genes in response to filarial antigens," *International Immunology* 9(7):955-962.

Zemlin et al. (Mar. 1, 2001). "The diversity of rearranged immunoglobulin heavy chain variable region genes in peripheral blood B cells of preterm infants is restricted by short third complementarity-determining regions but not by limited gene segment usage," *Blood* 97(5)1511-1513.

Driessen et al. (1999). "Primary diffuse large B cell lymphoma of the stomach: analysis of somatic mutations in the rearranged immunoglobulin heavy chain variable genes indicated antigen selection," *Leukemia* 13:1085-1092.

Kneba et al. (Nov. 15, 1995). "Analysis of Rearranged T-Cell Receptor β-Chain Genes by Polymerase Chain Reaction (PCR) DNA Sequencing and Automated High Resolution PCR Fragment Analysis," *Blood* 86(10):3930-3937.

Wu and Kabat. (1970). "An Analysis of the Sequences of the Variable Regions of Bence Jones Proteins and Myeloma Light Chains and their Implications for Antibody Complementarity," *Journal of Exp. Med.* 132(2):211-250.

Helmuth et al. (2000). "Germline repertoire of the immunoglobulin $V_H3$ family in rhesus monkeys," *Immunogenetics* 51:519-527.

Shimizudani et al. (2002). "Conserved CDR 3 region of T cell receptor BV gene in lymphocytes from bronchoalveolar lavage fluid of patients with idiopathic pulmonary fibrosis," *Clin. Exp. Immunol.* 129:140-149.

Doenecke et al. (1997). "Rapid amplification of cDNA ends (RACE) improves the PCR-based isolation of immunoglobulin variable region genes from murine and human lymphoma cells and cell lines," *Leukemia* 11:1787-1792.

McCarthy et al. (1990). "Rapid method for distinguishing clonal from polyclonal B cell populations in surgical biopsy specimens," *J. Clin. Pathol.* 43:429-432.

Reisman et al. (Jul. 1988). "Human p53 oncogene contains one promoter upstream of exon 1 and a second, stronger promoter within intron 1," *Proc. Natl. Acad. Sci.* 85:5146-5150.

Bentley and Groudine. (Oct. 1986). "Novel Promoter Upstream of the Human *c-myc* Gene and Regulation of *c-myc* Expression in B-Cell Lymphomas," *Molecular and Cellular Biology* 6(10):3481-3489.

Hernandez, Nouria. (1985). "Formation of the 3' end of U1 snRNA is directed by a conserved sequence located downstream of the coding region," *The EMBO Journal* 4(7):1827-1837.

Conway and Wickens. (Jun. 1985). "A sequence downstream of A-A-U-A-A-A is required for formation of simian virus 40 late mRNA 3" termini in frog oocytes," *Proc. Natl. Acad. Sci.* 82:3949-3953.

Weber et al. (1984). "Repetitive DNA sequences within and around the rat prolactin gene," *Molecular and Cellular Biochemistry* 65:171-179.

Söderström et al. (1999). "Altered VH6-D-JH repertoire in human insulin-dependent diabetes mellitus and autoimmune idiopathic thrombocytopenic purpura," *Eur. J. Immunol.* 29:2853-2862.

Varade et al. (Jun. 1, 1993). "Use of the Most $J_H$-Proximal Human Ig H Chain V Region Gene, $V_{H6}$, in the Expressed Immune Repertoire," *The Journal of Immunology* 150:4985-4995.

Altschul et al. (1990). "Basic Local Alignment Search Tool," *J. Mol. Biol.* 215:403-410.

Lefranc, Marie-Paule. (2002). "IMGT, the international ImMunoGeneTics database: a high-quality information system for comparative immunogenetics and immunology," *Developmental and Comparative immunology* 26:697-705.

Lefranc, Marie-Paule. (2001). "Nomenclature of the Human Immunoglobulin Heavy (IGH) Genes," *Exp Clin. Immunogenet.* 18:100-116.

Ruiz et al. (1999). "The Human Immunoglobulin Heavy Diversity (IGHD) and Joining (IGHJ) Segments," *Exp. Clin. Immunogenet.* 16:173-184.

Folch and Lefranc. (2000). "The Human T Cell Receptor Beta Diversity (TRBD) and Beta Joining (TRBJ) Genes," *Exp. Clin. Immunogenet.* 17:107-114.

Scaviner and Lefranc. (2000). "The Human T Cell Receptor Alpha Joining (TRAJ) Genes," *Exp Clin. Immunogenet.* 17:97-106.

Scaviner and Lefranc. (2000). "The Human T Cell Receptor Alpha Cariable (TRAV) Genes," *Exp. Clin. Immunogenet.* 17:83-96.

Cook and Tomlinson. (1995). "The human immunoglobulin $V_H$ repertoire," *Immunology Today* 16(5):237-242.

Tomlinson et al. (1992). "The Repertoire of Human Germline $V_H$ Sequences Reveals about Fifty Groups of $V_H$ Segments with Different Hypervariable Loops," *J. Mol. Biol.* 227:776-798.

Ravetch et al. (Dec. 1981). "Structure of the Human Immunoglobulin μ Locus: Characterization of Embryonic and Rearranged J and D Genes," *Cell* 27:583-591.

Gellrich et al. (1999). "Analysis of $V_H$-D-$J_H$ Gene Transcripts in B Cells Infiltrating the Salivary Glands and Lymph Node Tissues of Patients with Sjögren's Syndrome," *Arthritis & Rheumatism* 42(2):240-247.

Szczepanski et al. (Jun. 15, 1999). "Ig Heavy Chain Gene Rearrangements in T-Cell Acute Lymphoblastic Leukemia Exhibit Predominant $D_H6-19$ and $D_H7-27$ Gene Usage, Can Result in Complete V-D-J Rearrangements, and Are Rare in T-Cell Receptor αβ Lineage," *Blood* 93(12):4079-4085.

Corbett et al. (1997). "Sequence of the Human Immunoglobulin Diversity (D) Segment Locus: A Systematic Analysis Provides No Evidence for the Use of DIR Segments, Inverted D Segments, 'Minor' D Segments or D-D Recombination," *J. Mol. Biol.* 270:587-597.

"Immunoglobulin Heavy Variable Cluster: IGHV," located at <http://www.ncbi.nlm.nih.gov/entrez/dispomim.cgi?id=147070> visited on Apr. 6, 2007. (5 pages).

Butler et al. (2000). "Antibody Repertoire Development in Fetal and Neonatal Piglets. II. Characterization of Heavy Chain Complementarity-Determining Region 3 Diversity in the Developing Fetus," *The Journal of Immunology*: 6999-7010.

Brezinschek et al. (1995). "Analysis of the Heavy Chain Repertoire of Human Peripheral B Cells Using Single-Cell Polymerase Chain Reaction," *The Journal of Immunology*: 190-202.

Brezinschek et al. (May 1997). "Analysis of the Human VH Gene Repertoire," *J. Clin. Invest.* 99(10):2488-2501.

Brisco et al. (1994). "Outcome prediction in childhood acute lymphoblastic leukaemia by molecular quantification of residual disease at the end of induction," *Lancet* 343(8891):196-200.

Willenbrock et al. (May 2001). "Analysis of T-Cell Subpopulations in T-Cell Non-Hodgkin's Lymphoma of Angioimmunoblastic Lymphadenopathy with Dysproteinemia Type by Single Target Gene Amplification of T Cell Receptor-β Gene Rearrangements," *American Journal of Pathology* 158(5):1851-1857.

Obexer-Ruff et al. (1998). "Caprine T-Cell Receptor Variable β-Chain (TCRVβ) Repertoire Analysis and Potential Applications in Cowdriosis Immune Response Studies," *Annals of the New York Academy of Sciences* 849:321-326.

Manfras et al. (1999). "Non-productive Human TCR β Chain Genes Represent V-D-J Diversity before Selection upon Function: Insight into Biased Usage of TCRBD and TCRBJ Genes and Diversity of CDR3 Region Length," *Human Immunology* 60:1090-1100.

Hall and Launchbury. (1995). "Healthy Human T-Cell Receptor β-Chain Repertoire: Quantitative Analysis and Evidence for Jβ-Related Effects on CDR3 Structure and Diversity," *Human Immunology* 43:207-218.

Mancini et al. (1999). "TCR α-Chain Repertoire in pTα-Deficient Mice Is Diverse and Developmentally Regulated: Implications for Pre-TCR Functions and TCRA Gene Rearrangement," *The Journal of Immunology* 163: 6053-6059.

Hansen-Hagge et al. (1989). "Detection of Minimal Residual Disease in Acute Lymphoblastic Leukemia by In Vitro Amplification of Rearranged T-Cell Receptor δ Chain Sequences," *Blood* 74(5):1762-1767.

Tkachuk et al. (Jul. 1988). "Rearrangement of T-Cell δ Locus in Lymphoproliferative Disorders," *Blood* 72(1): 353-357.

Holtmeier et al. (1997). "The TCR-δ Repertoire in Human Intestine Undergoes Characteristic Changes During Fetal to Adult Development," *The Journal of Immunology* 158:5632-5641.

Gellrich et al. (Oct. 2000). "Microanatomical Compartments of Clonal and Reactive T Cells in Mycosis Fungoides: Molecular Demonstration by Single Cell Polymerase Chain Reaction of T Cell Receptor Gene Rearrangements," *The Journal of Investigative Dermatology* 115(4):620-624.

Lorenzen et al. (1996). "Single-cell Analysis of T-cell Receptor-γ Rearrangements in Large-cell Anaplastic Lymphoma," *Diagnostic Molecular Pathology* 5(1): 10-19.

Pardoll et al. (1987). "The unfolding story of T cell receptor γ," *FASEB Journal* 1(2): 103-109.

LeFranc et al. (Apr. 25, 1986). "Diversity and Rearrangement of the Human T Cell Rearranging γ Genes: Nine Germ-Line Variable Genes Belonging to Two Subgroups," *Cell* 45:237-246.

Lefranc et al. (Jan. 30, 1986). "Rearrangement of two distinct T-cell γ-chain variable-region genes in human DNA," *Nature* 319:420-422.

Nowak, Jerzy S. et al. (1997). "Limited Junctional Diversity of Vδ5-Jδ1 Rearrangement in Multiple Sclerosis Patients," *Molecular and Chemical Neuropathology*. 30:95-99.

Ma, Hongboo et al. (2000). "Multiplex Polymerase Chain Reaction-Based Analysis Of T-Cell Receptor γ Gene Rearrangements For The Determination Of T-Lymphocyte Clonality", *Enviornmental And Molecular Mutagenesis*. 35: 1-8.

Australian Office Action mailed on Feb. 22, 2008 directed at counterpart application No. 2004238887; 2 pages.

Chinese Office Action mailed on Mar. 21, 2008 directed at counterpart application No. 200480016603.5; 8 pages.

Supplementary European Search Report mailed on Feb. 6, 2008 directed at counterpart application No. 04732551.9; 3 pages.

\* cited by examiner

METHOD OF ANALYSING A MARKER NUCLEIC ACID MOLECULE

FIELD OF THE INVENTION

The present invention relates to a method of characterising a nucleic acid region and, more particularly, to a method of analysing a marker nucleic acid region. The method of the present invention is based on identification of one or both of the nucleic acid regions flanking a marker nucleic acid region and provides a means of analysing a marker nucleic acid region which is characteristic of a clonal population of cells. The method of the present invention is useful in the context of enabling a range of applications including, but not limited to, monitoring the progression of a condition characterised by the presence of a clonal populations of cells (such as a neoplastic condition), monitoring the levels of one or more clonal cell population, predicting the likelihood of a subject's relapse from a remissive state to a disease state, for assessing the effectiveness of existing therapeutic drugs and/or new therapeutic agents and identifying the presence of a marker region.

BACKGROUND OF THE INVENTION

The reference to any prior art in this specification is not, and should not be taken as, an acknowledgment or any form of suggestion that that prior art forms part of the common general knowledge in Australia.

A clone is generally understood as a population of cells which has descended from a common precursor cell. Diagnosis and/or detection of the existence of a clonal population of cells or organisms in a subject has generally constituted a relatively problematic procedure. Specifically, a clonal population may constitute only a minor component within a larger population of cells or organisms. For example, in terms of the mammalian organism, one of the more common situations in which detection of a clonal population of cells is required occurs in terms of the diagnosis and/or detection of neoplasms, such as cancer. However, detection of one or more clonal populations may also be important in the diagnosis of conditions such as myelodysplasia or polycythaemia vera and also in the detection of antigen driven clones generated by the immune system.

Generally, the population within which the clone arises corresponds to a population of cells within a particular tissue or compartment of the body. Nevertheless, despite the fact that sampling such a population of cells effectively narrows the examination to a sub group of cells or organisms, this may nevertheless still present a clinician with a large background population of non-clonal cells or organisms within which the clonal population must be identified.

If the members of the clone are characterized by a molecular marker, such as an altered sequence of DNA, then the problem of detection may be able to be translated into the problem of detecting a population of molecules which all have the same molecular sequence within a larger population of molecules which have a different sequence, either all being the same and different, or being heterogeneous to a greater or lesser extent. The level of detection of the marker molecules that can be achieved is very dependent upon the sensitivity and specificity of the detection method, but nearly always, when the proportion of target molecules within the larger population of molecules becomes small, the signal noise from the larger population makes it impossible to detect the signal from the target molecules.

Accordingly, there is a need to develop improved methods for qualitatively and/or quantitatively detecting the existence of a clonal population of cells within any biological context (ie. irrespective of the level of non-clonal background cellular material), which methods are highly sensitive yet simple to routinely perform.

In work leading up to the present invention, it has been determined that the marker sequence of interest, to which the detection method is directed, is situated in a single region of the genome and is usually flanked by unique sequences. In particular, it has been determined that the marker of interest is often flanked on one or both sides by unique sequences which correspond to one or two members of a family of repeated sequences. To the extent that the different members of each subject family of repeated sequences themselves differ in sequence, it has been determined that those sequences provide a unique means of analysing, for example characterising, detecting, isolating or quantifying, a marker sequence of interest. It has also been determined that such sequences can be routinely and simply identified by any suitable methods such as microassay-related methodology or PCR. In relation to the latter, for example, one can conduct a multiplicity of amplification reactions which each differ in the context of the primer pair comprising that reaction. Specifically, by designing primer pairs wherein one primer is common to all reactions and is directed to a conserved region, such as a consensus sequence, of one flanking sequence and the other primer is selected from a group of primers such that each individual member of the group is specific for each individual member of a family of repeated sequences, it can be clearly and easily determined which two members of the family of repeated sequences flank the marker nucleic acid molecule characterising the clonal population of interest. Such principles can also be applied in the context of other platform technologies, such as chip-based microassays which comprise an array of probes specifically directed to each member of a family of repeated sequences. The development of this method thereby facilitates a means of detecting and/or monitoring the subject clonal population of cells, even in the context of a large non-subject-clonal background cellular population, by providing a means of specifically enriching for said marker sequences utilising the primers identified in accordance with the method of the present invention.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The present invention is not to be limited in scope by the specific embodiments described herein, which are intended for the purposes of exemplification only. Functionally-equivalent products, compositions and methods are clearly within the scope of the invention, as described herein.

As used herein, the term "derived from" shall be taken to indicate that a particular integer or group of integers has originated from the species specified, but has not necessarily been obtained directly from the specified source.

The subject specification contains nucleotide sequence information prepared using the programme PatentIn Version 3.1, presented herein after the bibliography. Each nucleotide sequence is identified in the sequence listing by the numeric indicator <210> followed by the sequence identifier (eg. <210>1, <210>2, etc). The length, type of sequence (DNA, etc) and source organism for each nucleotide sequence are indicated by information provided in the numeric indicator fields <211>, <212> and <213>, respectively. Nucleotide sequences referred to in the specification are identified by the indicator SEQ ID NO: followed by the sequence identifier (eg. SEQ ID NO: 1, SEQ ID NO:2, etc.). The sequence identifier referred to in the specification correlates to the information provided in numeric indicator field <400> in the sequence listing, which is followed by the sequence identifier (eg. <400>1, <400>2, etc.). That is SEQ ID NO:1 as detailed in the specification correlates to the sequence indicated as <400>1 in the sequence listing.

One aspect of the present invention is directed to a method of analysing a marker nucleic acid region, which marker nucleic acid region is characteristic of a clonal population of cells and is flanked on one or both sides by members of a family of distinct repeated sequences, said method comprising identifying one or more of the nucleic acid sequence regions flanking said marker nucleic acid region.

In another aspect there is provided a method of analysing a marker DNA region, which marker DNA region is characteristic of a clonal population of cells and is flanked on one or both sides by members of a family of distinct repeated DNA sequences, said method comprising identifying one or more of the DNA regions flanking said marker DNA region.

In yet another aspect the present invention provides a method of analysing a variable region gene segment, which variable region gene segment is characteristic of a clonal population of lymphoid cells, said method comprising identifying said V and D gene family members.

In still another aspect the present invention provides a method of analysing a variable region gene segment, which variable region gene segment is characteristic of a clonal population of lymphoid cells, said method comprising identifying said V and J gene family members.

In yet still another aspect the present invention provides a method of analysing a variable region gene segment, which variable region gene segment is characteristic of a clonal population of lymphoid cells, said method comprising identifying said D and J gene family members.

In still yet another aspect the present invention provides a method of analysing a marker nucleic acid sequence region, which marker nucleic acid region is characteristic of a clonal population of cells and is flanked on one or both sides by members of a family of distinct repeated sequences, said method comprising:

(i) facilitating a multiplicity of amplification reactions of the nucleic acid molecules derived from said clonal cell population, said amplification reactions utilising a pair of primers wherein the first primer is common to all reactions and is directed to a conserved region of the upstream flanking sequence and the second primer is selected from a group of primers each specific for a member of said family of downstream repeated sequences;

(ii) identifying which of said second primers facilitates amplification of said flanking sequence;

(iii) repeating steps (i) and (ii) wherein said first primer is common to all reactions and is directed to a conserved region of the downstream flanking sequence and said second primer is selected from a group of primers each specific for an upstream member of said family of repeated sequences.

In a further aspect the present invention provides a method of analysing a marker nucleic acid sequence region, which marker nucleic acid region is characteristic of a clonal population of cells and is flanked on one or both sides by members of a family of distinct repeated sequences, said method comprising:

(i) facilitating a multiplicity of amplification reactions of the nucleic acid molecules derived from said clonal cell population, said amplification reactions utilising a pair of primers wherein the first primer is selected from a group of primers each specific for a member of said upstream family of repeated sequences and the second primer is selected from a group of primers each specific for a member of said downstream family of repeated sequences; and (ii) identifying which of said first and second primers facilitates amplification of said flanking sequence.

In still another further aspect there is provided a method of analysing a marker nucleic acid sequence region, which marker nucleic acid region is characteristic of a clonal population of cells and is flanked on one or both sides by members of a family of distinct repeated sequences, said method comprising:

(i) facilitating a multiplicity of polymerase chain amplification reactions of the nucleic acid molecules derived from said clonal cell population, said amplification reactions utilising a pair of primers wherein the first primer is common to all reactions and is directed to a conserved region of the upstream flanking sequence and the second primer is selected from a group of primers each specific for a member of said downstream family of repeated sequences;

(ii) identifying which of said second primers facilitates amplification of said flanking sequence;

(iii) repeating steps (i) and (ii) wherein said first primer is common to all reactions and is directed to a conserved region of the downstream flanking sequence and said second primer is selected from a group of primers each specific for an upstream member of said family of repeated sequences.

In yet still another aspect the present invention provides a method of analysing a marker nucleic acid sequence region, which marker nucleic acid region is characteristic of a clonal population of cells and is flanked on one or both sides by members of a family of distinct repeated sequences, said method comprising:

(i) facilitating a multiplicity of polymerase chain amplification reactions of the nucleic acid molecules derived from said clonal cell population, said amplification reactions utilising a pair of primers wherein the first primer is selected from a group of primers each specific for a member of said upstream family of repeated sequences and the second primer is selected from a group of primers each specific for a member of said downstream family of repeated sequences; and (ii) identifying which of said first and second primers facilitates amplification of said flanking sequence.

In yet still another further aspect there is provided a method of monitoring a clonal population of cells in a mammal, which clonal cells are characterised by a marker nucleic acid molecule and which marker nucleic molecule is flanked on one or both sides by sequences which are members of a family of distinct repeated sequences in accordance with the methods hereinbefore described.

DETAILED DESCRIPTION OF THE INVENTION

Figure 1:
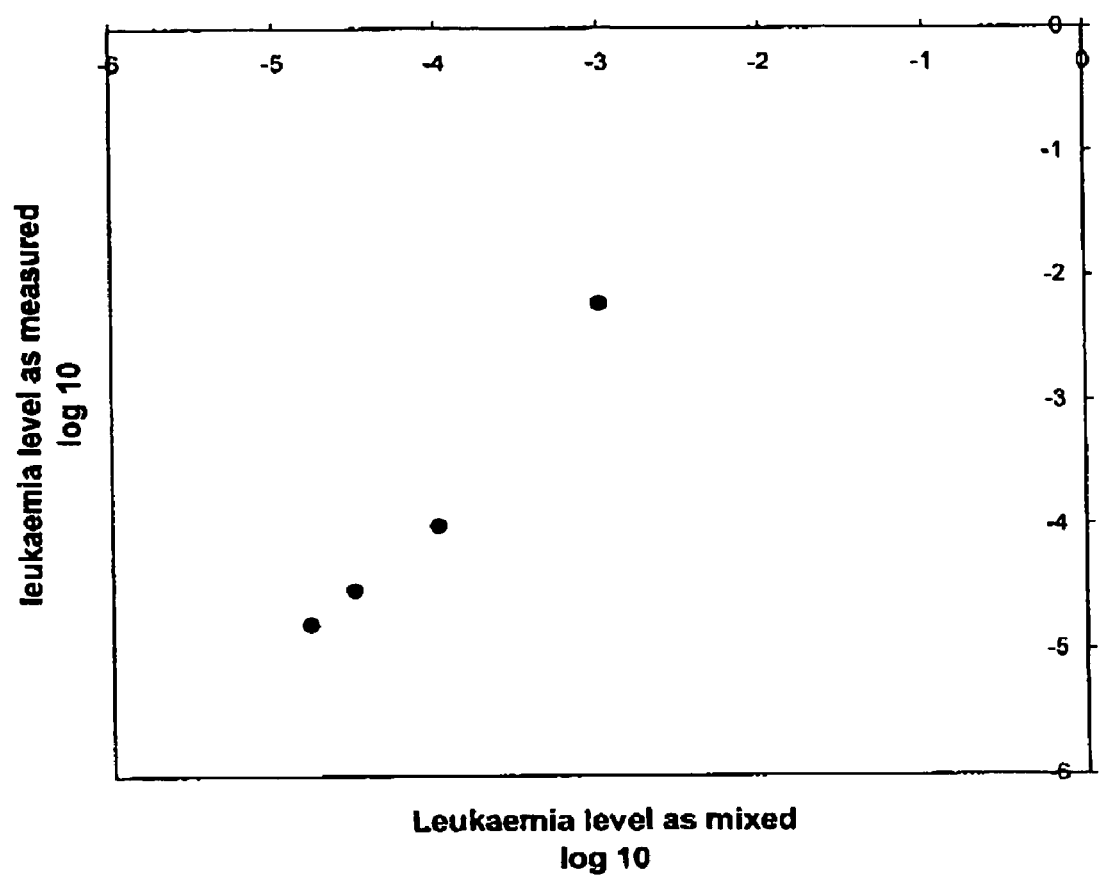
FIG. 1 is a graphical representation of the quantification of leukaemia using primers binding to flanking sequences.

The present invention is predicated, in part, on the development of a simple yet highly accurate method of analysing a marker nucleic acid region, in particular the marker nucleic acid region which distinguishes a clonal population of cells of interest. Specifically, it has been determined that a marker nucleic acid region can be accurately characterised, and its routine analysis thereby facilitated, in terms of the nucleic acid regions which flank the marker region. This method is particularly valuable where the marker nucleic acid region is flanked by members of a family of distinct repeated sequences which differ from one another in terms of actual nucleic acid sequence. This now provides a means for reducing non-marker background sequences which may be present in a test sample, thereby facilitating monitoring of the progression of a condition characterised by the expansion of a clonal population of cells, predicting the likelihood of a subject's relapse from a remissive state or disease state or for assessing the effectiveness of existing therapeutic drugs and/ or new therapeutic agents.

Accordingly, one aspect of the present invention is directed to a method of analysing a marker nucleic acid region, which marker nucleic acid region is characteristic of a clonal population of cells and is flanked on one or both sides by members of a family of distinct repeated sequences, said method comprising identifying one or more of the nucleic acid sequence regions flanking said marker nucleic acid region.

Reference to "cells" should be understood as a reference to all forms of cells from any species and to mutants or variants thereof. Without limiting the present invention to any one theory or mode of action, a cell may constitute an organism (in the case of unicellular organisms) or it may be a subunit of a multicellular organism in which individual cells may be more or less specialised (differentiated) for particular functions. All living organisms are composed of one or more cells. The subject cell may form part of the biological sample, which is the subject of testing, in a syngeneic, allogeneic or xenogeneic context. A syngeneic process means that the clonal cell population and the biological sample within which that clonal population exists share the same MHC genotype. This will most likely be the case where one is screening for the existence of a neoplasia in an individual, for example. An "allogeneic" process is where the subject clonal population in fact expresses a different MHC to that of the individual from which the biological sample is harvested. This may occur, for example, where one is screening for the proliferation of a transplanted donor cell population (such as an immunocompetent bone marrow transplant) in the context of a condition such as graft versus host disease. A "xenogeneic" process is where the subject clonal cells are of an entirely different species to that of the subject from which the biological sample is derived. This may occur, for example, where a potentially neoplastic donor population is derived from xenogeneic transplant.

"Variants" of the subject cells include, but are not limited to, cells exhibiting some but not all of the morphological or phenotypic features or functional activities of the cell of which it is a variant. "Mutants" includes, but is not limited to, cells which have been naturally or non-naturally modified such as cells which are genetically modified.

By "clonal" is meant that the subject population of cells has derived from a common cellular origin. For example, a population of neoplastic cells is derived from a single cell which has undergone transformation at a particular stage of differentiation. In this regard, a neoplastic cell which undergoes further nuclear rearrangement or mutation to produce a genetically distinct population of neoplastic cells is also a "clonal" population of cells, albeit a distinct clonal population of cells. In another example, a T or B lymphocyte which expands in response to an acute or chronic infection or immune stimulation is also a "clonal" population of cells within the definition provided herewith. In yet another example, the clonal population of cells is a clonal microorganism population, such as a drug resistant clone which has arisen within a larger microorganismal population. Preferably, the subject clonal population of cells is a neoplastic population of cells or a clonal immune cell population.

The subject cells are characterised by a "marker nucleic acid region" Reference to a "marker nucleic acid region" which is characteristic of the subject clonal cell population should be understood as a reference to a nucleic acid molecule sequence (such as a unique gene or gene region sequence) which is found in the clonal cell but which is either not found in non-clonal cells or is not found in significant numbers in non-clonal cells. By "significant" is meant that the detection of the subject marker nevertheless provides a useful indicator of the clonal cells which are present in the subject sample. The marker preferably corresponds to a discrete nucleic acid molecule region and, therefore, may correspond to one or more genes or a part of a gene. The subject gene may not necessarily encode a protein but may correspond to a non-coding sequence which is nevertheless characteristic of the subject clonal cells.

The marker region may also correspond to a specific gene rearrangement. For example the marker may correspond to the rearranged genomic variable region nucleic acid molecule of a T cell receptor (herein referred to as "TCR≅) chain or an immunoglobulin chain. Without limiting the present invention in any way, each lymphoid cell undergoes somatic recombination of its germ line variable region gene segments (either V and J or V, D and J segments) depending on the particular gene rearranged in order to generate a total antigen diversity of approximately $10^{16}$ distinct variable region structures. In any given lymphoid cell, such as a T cell or B cell, at least two distinct variable region gene segment rearrangements are likely to occur due to the rearrangement of two or more of the two chains comprising the TCR or immunoglobulin molecule. Specifically, the $\alpha$, $\beta$, $\gamma$ or $\delta$ chains of the TCR and/or the heavy and light chains of the immunoglobulin molecule. In addition to rearrangements of the VJ or VDJ segment of any given immunoglobulin or TCR gene, nucleotides are randomly removed and/or inserted at the junction between the segments. This leads to the generation of enormous diversity.

The marker region may be DNA or RNA, such as mRNA, or derivative or analogue thereof. Where the marker region is a DNA molecule which encodes a proteinaceous molecule, its expression may be constitutive or it may require that a stimulatory signal be received by the cell in order to induce its transcription and translation. Since the method of the present invention is directed to screening for the marker nucleic acid region per se, where genomic DNA is the subject of detection it is not material whether the marker is expressed or not. However, if the subject method is directed to detecting mRNA, and the protein encoded by said marker is not constitutively produced, it will be necessary to suitably stimulate the subject cell prior to screening. Such stimulation may be performed either in vitro after the biological sample comprising the subject cells has been harvested from the mammal or a stimulatory signal may be administered to the mammal prior to harvesting of the biological sample. Still further, the marker nucleic acid region may be one which is normally found in the subject cell prior to its clonal expansion. Alternatively, the marker may be a mutation which occurs in the subject cell at the time of its clonal expansion. For example, where neoplastic transformation is induced by viral infection of a non-neoplastic cell, the subject marker may be a virus derived or virus specific molecule.

Preferably, said marker nucleic acid region is a marker DNA region.

The present invention therefore more particularly provides a method of analysing a marker DNA region, which marker DNA region is characteristic of a clonal population of cells and is flanked on one or both sides by members of a family of distinct repeated DNA sequences, said method comprising identifying one or more of the DNA regions flanking said marker DNA region.

The method of the present invention is directed to identifying the nucleic acid sequence regions which flank the subject marker region. Reference to a "flanking" sequence is intended as a reference to a nucleic acid sequence which is located proximally to the marker nucleic acid region. By "proximally to" is meant that the sequences are positioned relative to the marker region such that their identification provides a useful means for analysis or study of a subject clonal population. Preferably, said flanking sequences are located near to or immediately adjacent to the terminal ends of the subject marker region. It should be understood that to the extent that the marker region is a discrete gene or region of the gene, the flanking sequences are located proximally to that gene. However, it should be understood that to the extent that the marker region is defined by a genomic rearrangement event, the subject flanking sequences may comprise sequences flanking the group of rearranged genes (eg. the rearranged VJ or VDJ genes of a T or B cell) or, preferably, the flanking sequences may correspond to the rearranged genes themselves, such as the VJ, VD or DJ genes. In this case, the marker can be thought of as corresponding to the unique junction which is created between the rearranged VJ, VD or DJ genes. The subject flanking sequences may be a gene or part of a gene.

As detailed hereinbefore, the flanking sequences which are the subject of identification in accordance with the method of the present invention are those which are members of a family of distinct repeated sequences. By "family of distinct repeated sequences" is meant that a group of nucleic acid sequences, preferably genes, exhibit a level of homology high enough that they can be categorised as members of a single class of gene, but which members nevertheless exhibit unique differences in their actual nucleic acid sequence. It should be understood that where there are two flanking sequences in issue, these may be members of the same family of repeated sequences or they may be members of two different families of repeated sequences. Preferably, the subject family sequences are ones which are members of the immunoglobulin or T cell variable region receptor gene family (ie. the various V, D and J members), ribosomal RNA genes, HOX genes, repetitive elements such as Alu or MHC genes.

Preferably, said clonal cell is a lymphoid cell and said marker is a rearranged variable region gene segment.

Accordingly, a preferred embodiment of the present invention provides a method of analysing a variable region gene segment, which variable region gene segment is characteristic of a clonal population of lymphoid cells, said method comprising identifying said V and D gene family members.

Another preferred embodiment of the present invention provides a method of analysing a variable region gene segment, which variable region gene segment is characteristic of a clonal population of lymphoid cells, said method comprising identifying said V and J gene family members.

Yet another preferred embodiment the present invention provides a method of analysing a variable region gene segment, which variable region gene segment is characteristic of a clonal population of lymphoid cells, said method comprising identifying said D and J gene family members.

It should be understood that reference to "lymphoid cell" is a reference to any cell which has rearranged at least one germ line set of immunoglobulin or TCR variable region gene segments. The immunoglobulin variable region encoding genomic DNA which may be rearranged includes the variable regions associated with the heavy chain or the $\kappa$ or $\lambda$ light chain while the TCR chain variable region encoding genomic DNA which may be rearranged include the $\alpha$, $\beta$, $\gamma$ and $\delta$ chains. In this regard, a cell should be understood to fall within the scope of the "lymphoid cell" definition provided the cell has rearranged the variable region encoding DNA of at least one immunoglobulin or TCR gene segment region. It is not necessary that the cell is also transcribing and translating the rearranged DNA. In this regard, "lymphoid cell" includes within its scope, but is in no way limited to, immature T and B cells which have rearranged the TCR or immunoglobulin variable region gene segments but which are not yet expressing the rearranged chain (such as TCR$^-$ thymocytes) or which have not yet rearranged both chains of their TCR or immunoglobulin variable region gene segments. This definition further extends to lymphoid-like cells which have undergone at least some TCR or immunoglobulin variable region rearrangement but which cell may not otherwise exhibit all the phenotypic or functional characteristics traditionally associated with a mature T cell or B cell. Accordingly, the method of the present invention can be used to monitor neoplasias of cells including, but not limited to, lymphoid cells at any differentiative stage of development, activated lymphoid cells or non-lymphoid/lymphoid-like cells provided that rearrangement of at least part of one variable region gene region has occurred. It can also be used to monitor the clonal expansion which occurs in response to a specific antigen.

It should also be understood that although it is preferable that the rearrangement of at least one variable region gene region has been completed, the method of the present invention is nevertheless applicable to monitoring neoplastic cells which exhibit only partial rearrangement. For example, a B cell which has only undergone the DJ recombination event is a cell which has undergone only partial rearrangement. Complete rearrangement will not be achieved until the DJ recombination segment has further recombined with a V segment. The method of the present invention can therefore be designed to detect the partial or complete variable region rearrangement of one TCR or immunoglobulin chain utilising a reference molecule complementary to this marker sequence or, for example, if greater specificity is required and the neoplastic cell has rearranged the variable region of both TCR or immunoglobulin chains, primer molecules directed to both forms of rearrangement can be utilised.

As detailed hereinbefore, reference to a "nucleic acid" should be understood as a reference to both deoxyribonucleic acid and ribonucleic acid or derivatives or analogues thereof. In this regard, it should be understood to encompass phosphate esters of ribonucleotides and/or deoxyribonucleotides, including DNA (cDNA or genomic DNA), RNA, mRNA or tRNA among others. The nucleic acid molecule comprising the marker and flanking sequences may be naturally occurring or it may be the result of non-natural events such as the recombinant engineering of the subject clonal cell, for example a cell which has earlier been the subject of a genetic therapeutic regime. In terms of the probe or primer molecules which would likely be utilised to identify the flanking sequences, it should be understood that these nucleic acid molecules encompass reference to derivatives or analogues of nucleic acid molecules.

Reference to "derivatives" should be understood to include reference to fragments, parts, portions, chemical equivalents, analogues, mutants, homologous and mimetics from natural, synthetic or recombinant sources. "Functional derivatives" should be understood as derivatives which exhibit any one or more of the functional activities of nucleotides or nucleic acid sequences. The derivatives of said nucleotides or nucleic acid sequences (eg. said marker region or said primers) include fragments having particular epitopes or parts of the nucleotide or nucleic acid sequence fused to other proteinaceous or non-proteinaceous molecules. The subject nucleic acid molecules (for the primers) may be fused to tags, for example which facilitate the isolation or detection of said molecules. Analogs contemplated herein include, but are not limited to, modifications to the nucleotide or nucleic acid sequence such as modifications to its chemical makeup or overall conformation. This includes, for example, modification to the manner in which nucleotides or nucleic acid sequences interact with other nucleotides or nucleic acid sequences such as at the level of backbone formation or complementary base pair hybridisation. The biotinylation of a nucleotide or nucleic acid sequence is an example of a "functional derivative" as herein defined. Derivatives of nucleic acid sequences may be derived from single or multiple nucleotide substitutions, deletions and/or additions. The term "functional derivatives" should also be understood to encompass nucleotides or nucleic acid sequences exhibiting any one or more of the functional activities of a nucleotide or nucleic acid sequence, such as for example, products obtained following natural product screening and also to encompass nucleotide sequences on different backbones such as peptide nucleic acids.

Reference to "identifying" in the context of identifying the nucleic acid sequence regions flanking a marker nucleic acid region should be understood as a reference to determining sufficient of the nucleic acid sequence information of the subject flanking region such that there is facilitated identification and/or isolation/enrichment and/or quantification of the marker region and, by implication, the clonal population of cells of interest. The subject flanking regions may be identified by any suitable technique including, but not limited to:

(i) microarray technology which utilizes a multiplicity of in parallel hybridization reactions to a series of probes ordered on a solid surface such as a chip or a slide. Each individual probe, or a subset of the probes has specificity for a different individual member of a family of flanking sequences. By determining the pattern of hybridization, the member of the family which flanks the marker sequence can be identified, usually as the most 3 prime V family probe showing hybridization, as the most 5 prime J family probe showing hybridization and as the D probe which shows greatest hybridization.

(ii) nucleic acid sequencing technology directed to identifying the flanking and/or nucleic acid regions. Any suitable form of sequencing technology may be utilised including, but not limited to, pyrosequencing and minisequencing.

(iii) nucleic acid amplification technology (such as PCR) which utilises a multiplicity of amplification reactions, each characterised by the use of a unique combination of primer molecules directed either to specific members of the putative flanking region family or to a consensus sequence thereof, in order to identify one or both of the regions flanking a marker nucleic acid region of interest.

For example, one may perform a multiplicity of amplification reactions utilising a pair of primers wherein the first primer is common to all reactions and is directed to the flanking sequence upstream of the marker region and the second primer is selected from a group of primers each specific for a member of the family of repeated sequences located on the downstream side of the marker region. These reactions are also performed in the opposite design wherein the first primer is directed to the downstream flanking sequence and the second primer is directed to the upstream flanking sequence. Alternatively, the above steps can be combined by performing a large multiplicity of amplification reactions each involving the use of first and second primers directed to a specific member of an upstream flanking sequence family and a specific member of a downstream flanking sequence family. In this type of amplification design, the totality of amplification reactions cover all the different combinations of upstream and downstream primers. By designing and performing a single experiment which contains all the combinations of the individual members of the two families one does more PCR reactions. However, these reactions are performed as a single step procedure, which may provide significant advantages where one is working with smaller clonal populations.

(iii) DNA sequencing which determines the flanking sequences directly.

Preferably, the subject technique is nucleic acid amplification technology.

According to one preferred embodiment the present invention provides a method of analysing a marker nucleic acid sequence region, which marker nucleic acid region is characteristic of a clonal population of cells and is flanked on one or both sides by members of a family of distinct repeated sequences, said method comprising:

(i) facilitating a multiplicity of amplification reactions of the nucleic acid molecules derived from said clonal cell population, said amplification reactions utilising a pair of primers wherein the first primer is common to all reactions and is directed to a conserved region of the upstream flanking sequence and the second primer is selected from a group of primers each specific for a member of said downstream family of repeated sequences;

(ii) identifying which of said second primers facilitates amplification of said flanking sequence;

(iii) repeating steps (i) and (ii) wherein said first primer is common to all reactions and is directed to a conserved region of the downstream flanking sequence and said second primer is selected from a group of primers each specific for an upstream member of said family of repeated sequences.

According to another preferred embodiment the present invention provides a method of analysing a marker nucleic acid sequence region, which marker nucleic acid region is characteristic of a clonal population of cells and is flanked on one or both sides by members of a family of distinct repeated sequences, said method comprising:

(i) facilitating a multiplicity of amplification reactions of the nucleic acid molecules derived from said clonal cell population, said amplification reactions utilising a pair of primers wherein the first primer is selected from a group of primers each specific for a member of said upstream family of repeated sequences and the second primer is selected from a group of primers each specific for a member of said downstream family of repeated sequences; and (ii) identifying which of said first and second primers facilitates amplification of said flanking sequence.

In accordance with the preferred embodiments, said clonal cell is a lymphoid cell and said marker is a rearranged variable region gene segment.

Most preferably, said family of distinct repeated sequences are the V and D families of sequences, the V and J families of sequences or the D and J families of sequences. In this regard, it should be understood that the up and downstream flanking sequences may be the same or different members of the same family of repeated sequences or they may be members of different families of repeated sequences.

The identification of flanking sequences in accordance with these preferred methods of the present invention is predicated on running a series of amplification reactions which are each directed to determining whether one specific member of the family of distinct repeated sequences corresponds to the member which is flanking the marker region of the clonal population of interest. In this regard, reference to "amplification" should be understood as reference to any method of amplifying a nucleic acid molecule, which methods would be well known to those of skill in the art. Preferably, said amplification is the polymerase chain reaction.

According to this preferred embodiment, there is provided a method of analysing a marker nucleic acid sequence region, which marker nucleic acid region is characteristic of a clonal population of cells and is flanked on one or both sides by members of a family of distinct repeated sequences, said method comprising:

(i) facilitating a multiplicity of polymerase chain amplification reactions of the nucleic acid molecules derived from said clonal cell population, said amplification reactions utilising a pair of primers wherein the first primer is common to all reactions and is directed to a conserved region of the upstream flanking sequence and the second primer is selected from a group of primers each specific for a member of said downstream family of repeated sequences;

(ii) identifying which of said second primers facilitates amplification of said flanking sequence;

(iii) repeating steps (i) and (ii) wherein said first primer is common to all reactions and is directed to a conserved region of the downstream flanking sequence and said second primer is selected from a group of primers each specific for an upstream member of said family of repeated sequences.

In another preferred embodiment the present invention provides a method of analysing a marker nucleic acid sequence region, which marker nucleic acid region is characteristic of a clonal population of cells and is flanked on one or both sides by members of a family of distinct repeated sequences, said method comprising:

(i) facilitating a multiplicity of polymerase chain amplification reactions of the nucleic acid molecules derived from said clonal cell population, said amplification reactions utilising a pair of primers wherein the first primer is selected from a group of primers each specific for a member of said upstream family of repeated sequences and the second primer is selected from a group of primers each specific for a member of said downstream family of repeated sequences; and (ii) identifying which of said first and second primers facilitates amplification of said flanking sequence.

In accordance with the preferred embodiments, said clonal cell is a lymphoid cell and said marker is a rearranged variable region gene segment.

Most preferably, said family of distinct repeated sequences are the V and D families of sequences, the V and J families of sequences or the D and J families of sequences. In this regard, it should be understood that the up and downstream flanking sequences may be the same or different members of the same family of repeated sequences or they may be members of different families of repeated sequences.

The amplification of this preferred embodiment of the present invention is predicated on utilising a pair of primers. Reference to a "primer" nucleic acid sequence should be understood as a reference to any molecule comprising a sequence nucleotides, or functional derivatives thereof, the function of which includes the hybridisation of at least one region of said nucleotide sequence with a target nucleic acid molecule. Derivatives may include derivatives such as locked nucleic acid, either of DNA or RNA, which have been modified in such a manner as to enhance or diminish hybridization. Accordingly, reference to a "target nucleic acid molecule" is a reference to any molecule comprising a sequence of nucleotides or functional derivatives thereof which molecule is a molecule of interest, specifically the flanking sequence, and is therefore the subject of identification via what is effectively an initial probing step. Both the nucleic acid primer and the target nucleic acid sequence may comprise non-nucleic acid components. For example, the nucleic acid primer may also comprise a non-nucleic acid detection tag, such as a fluorescent tag, or some other non-nucleic acid component which may facilitate certain aspects of the amplification process or analysis of the results derived therefrom. Similarly, the target nucleic acid sequence may comprise a non-nucleic acid component. For example, the target nucleic acid sequence may be bound to an antibody. This may occur, for example, where the target nucleic acid sequence, that is, the flanking sequence, is present in a biological sample isolated from an individual who is mounting an immune response, such as autoimmune response at the nuclear level, to said flanking sequence. In another example, the nucleic acid primer may be a protein nucleic acid which comprises a peptide backbone accepting nucleic acid sidechains.

The primer is preferably a single stranded nucleotide sequence and may have any conformation including, for example, a linear conformation or an open circle conformation, that is, where the nucleotide primer is substantially circular in shape but its terminal regions do not connect. Reference to the "terminal regions" of the nucleic acid primer is a reference to the regions located at each end of the primer.

Contacting the primer with the nucleic acid molecule population derived from said clonal population such that interaction is facilitated with any flanking sequence present in the test sample may be performed by any suitable method. These methods will be known to those skilled in the art. In this regard, reference to "interaction" should be understood as a reference to any form of interaction such as hybridisation between complementary nucleotide base pairs or some other form of interaction such as the formation of bonds between nucleic acid portions of the subject nucleic acid molecules. The interaction may occur via the formation of bonds such as, but not limited to, covalent bonds, hydrogen bonds, Van der Waal=s forces or any other mechanism of interaction. All references herein to "hybridisation" between two nucleic acid molecules should be understood to encompass any form of interaction between said molecules. In order to facilitate this interaction, it is preferable that both the primer and the target nucleic acid molecules are rendered partially or fully single stranded for a time and under conditions sufficient for hybridisation between a single stranded primer and a single stranded flanking sequence to occur.

Without limiting the theory or mode of operation of the present invention in any way, contacting the nucleic acid molecule population, derived from the clonal population of interest, with the primer molecules under hybridisation conditions will result in the formation of duplexes which will lead to amplification of the flanking sequences, and by definition the intervening marker sequence, in accordance with whatever amplification methodology is utilised. In this regard, the present invention is predicated on the establishment of a series of separate amplification reactions (a "multiplicity" of amplification reactions) which are designed to identify the downstream and/or the upstream flanking sequence. Reference to "downstream" and "upstream" are references to the position of the flanking sequences relative to the marker region. In this regard, it is generally understood that a downstream sequence is a sequence which appears on the 3' side of the marker region while an upstream region is one which is located on the 5' side of the marker region.

Following hybridization of the primers with the target nucleic acid molecules, extension occurs as a result of action of the enzyme DNA polymerase. In order to identify optimally which particular member of a family of repeat sequences flanks the marker sequence, it is optimal that primer binding and extension be as specific as possible for the primer which identifies that member of the family. Measures to enhance specificity and inhibit non-specific hybridization and extension will be known to those familiar with the art. They include optimization of the conditions of the amplification reaction and may include use of locked nucleic acids, especially at the 3 prime end of the primer.

In order to identify, in a simple yet efficient manner, the particular nucleic acid regions flanking a marker region of a clonal population of interest, the amplification reactions are set up such that a series of reactions are performed to determine the nature of the upstream flanking sequence and a parallel series of reactions are designed to detect the nature of the downstream flanking sequence. In terms of the upstream flanking sequence, in the first mentioned preferred embodiment of the present invention the amplification reactions are set up such that each reaction comprises a common primer which is directed to a conserved region of a downstream flanking sequence. By "conserved region" is meant a region which is common to all members of the family to which that flanking sequence belongs. Preferably, the subject conserved region is a consensus sequence. Since the flanking regions of the present invention are known families of sequences, the determination of a consensus sequence is a matter of routine procedure to one of skill in the art. In order to identify the nature of the upstream flanking region, each of these amplification reactions (which utilise a common downstream primer) will, in fact, each separately utilise a primer directed to a selected member of the family to which the upstream flanking sequence belongs. Preferably, sufficient amplification reactions will be established such that primers directed to each member of that family can be tested in the context of the nucleic acid population of interest. Subsequently to amplifying each of these reactions, only one reaction, being the reaction which included the primer specific to the upstream flanking region, will have resulted in the production of amplified product. The reactions which utilise primers directed to other members of the family from which the upstream flanking sequence derives will not have resulted in the generation of amplification products. The second mentioned preferred embodiment of the present invention operates on the same principle, except that all the primers which are utilised are directed to specific members of the family of repeated sequences. It should be understood, however, that although it is preferable that the method of the present invention be performed utilising a multiplicity of amplification reactions which screen for each and every member of the family of a given flanking sequence, it may not necessarily be the case that the establishment of a multiplicity of amplification reactions on such a large scale is required. For example, certain genetic families are known to preferentially express some members of that family more commonly than other members. Accordingly, it may be that the person of skill in the art would initially design a series of amplification reactions directed to testing these most commonly expressed gene members prior to proceeding with a series of reactions to test the less commonly expressed members in the event that a negative result is obtained from the first set of reactions.

The methodology described above provides a means of determining the specific nature of the upstream flanking sequence. However, as detailed hereinbefore, it is an object of the present invention to identify both the upstream and the downstream flanking sequences in order to provide a means of routinely monitoring a population of cells expressing a marker region flanked by these specific gene sequences. Accordingly, the present invention encompasses the design and performance of a further series of amplification reactions which are designed conversely to those detailed above. That is, this further series of reactions are designed to identify the specific nature of the downstream flanking sequence, in terms of which member of a family of repeated sequences it corresponds to, by utilising a primer directed to a conserved region of the upstream flanking sequence in each of these amplification reactions together with a primer specifically directed to one member of the family of repeated sequences for the identification of the downstream flanking sequence. As detailed in relation to the identification of the upstream flanking sequence, although it is preferable that a series of amplification reactions be set up which test for each and every member of a family of repeated sequences, it should be understood that the amplification reactions may be designed such that only some of the members are tested for in the first instance.

It should also be understood that although it is preferable that one identifies the flanking sequences both up and downstream of the marker sequence, the method of the present invention includes identifying only one of the flanking sequences. This may occur, for example, if a marker region is flanked on only one side by a member of a family of repeated sequences.

Means of executing the amplification reactions and determining which reactions have resulted in the production of an amplification product would be well known to those of skill in the art.

The present invention is predicated on analysing the nucleic acid population derived from a clonal cell population. For many types of analysis, identification of flanking sequences will be performed most simply by studying a pure clonal cell population or, at the very least, a cell population which is effectively pure. By "effectively pure" is meant that any contaminating non-clonal cells are of a sufficiently low level that the method of the present invention can still deliver an accurate result. In terms of isolating a clonal population, it should be understood that there are many disease conditions in which the harvesting of a suitable biological sample will effectively result in the harvesting of a population of cells comprising only the clonally expanded cell population. For example, many forms of leukemia are characterised by the existence of an effectively pure population of the leukemic population in the diagnostic material which is harvested from the patient. For some uses of the present invention, it may be necessary to effect one or more purification steps as a cell sample prior to performing the method of the present invention. For example, to the extent that a blood sample may comprise a population of neoplastic myeloid cells together with a normal heterogeneous population of non-myeloid cells, one may seek to sort the blood sample according to CD34 expression such that the myeloid cells are separated from the non-myeloid cells at the preliminary purification step. Such separation techniques can be routinely performed utilising techniques such as fluorescence activated cell sorting.

Nevertheless, for types of analysis in which multiple different clones in a cell sample are being analysed, a pure clonal population is not necessary. The sequences flanking the marker region of each clone can be identified by each specific pair of primers which results in amplification of the marker nucleic acid of that clone. In a real sense, the specific flanking sequences form part of the marker sequence but, if desired, additional analysis can be performed on the amplified products by analysing marker sequences internal to the flanking sequences either subsequent to amplification or even as part of the same amplification reaction.

The cell sample which is tested in accordance with the method of the present invention may be derived from any suitable source including both in vitro and in vivo sources. To the extent that a clonal cell population is derived from an in vivo source, it may be derived from any biological organism. In this regard, the biological sample may be derivable from any human or non-human organism. Non-human organisms contemplated by the present invention include primates, livestock animals (eg. sheep, pigs, cows, horses, donkeys), laboratory test animals (eg. mice, hamsters, rabbits, rats, guinea pigs), domestic companion animals (eg. dogs, cats), birds (eg. chicken, geese, ducks and other poultry birds, game birds, emus, ostriches), captive wild or tamed animals (eg. foxes, kangaroos, dingoes), reptiles, fish or prokaryotic organisms. Non-human organisms also include plant sources such as rice, wheat, maize, barley or canola. In terms of plant organisms, the method of the present invention is particularly useful, for example, for identifying the colonisation of a plant by either a desirable or undesirable cellular population or the uncontrolled proliferation of a cellular subpopulation.

It should be understood that the biological sample may be any sample of material derived from the organism. This includes reference to both samples which are naturally present in the organism, such as tissue and body fluids in a mammal (for example biopsy specimens such as lymphoid specimens, blood, lymph fluid, faeces or bronchial secretions) and samples which are introduced into the body of the organism and subsequently removed, such as, for example, the saline solution extracted from the lung following a lung lavage or from the colon following an enema. To the extent that the subject biological sample is a plant organism, the biological sample includes reference to propagation material thereof.

The biological sample which is tested according to the method of the present invention may be tested directly or may require some form of treatment prior to testing. For example, a biopsy sample may require homogenisation prior to testing. Where the sample comprises cellular material, it may be necessary to extract or otherwise expose the nucleic acid material present in the cellular material in order to facilitate analysis of the nucleic acid material. The sample may also require some form of stimulation prior to testing if the test is designed to detect an mRNA marker flanking sequence. In yet another example, the sample may be partially purified or otherwise enriched prior to analysis. For example, to the extent that a biological sample comprises a very diverse cell population, it may be desirable to select out a sub-population of particular interest. For example, and as detailed hereinbefore, to the extent that one is screening for the development of acute myeloid leukaemnia, a $CD34^+$ enriched blood sample provides a means of isolating the myeloid cell component of the blood sample for further analysis. This minimises, to a functionally insignificant level, the number of cell types which are analysed, by eliminating non-myeloid cells. In another example, it may be desirable to amplify the marker nucleic acid population prior to testing, where specific primers are available, or to amplify the nucleic acid population of the test sample as a whole utilising universal primers, for the purpose of providing a larger starting population of nucleic acid molecules.

The choice of what type of sample is most suitable for testing in accordance with the method disclosed herein will be dependent on the nature of the condition which is being monitored. For example, if a neoplastic condition is a lymphoid leukaemia, a blood sample, lymph fluid sample or bone marrow aspirate would likely provide a suitable testing sample. Where the neoplastic condition is a lymphoma, a lymph node biopsy or a blood or marrow sample would likely provide a suitable source of tissue for testing. Consideration would also be required as to whether one is monitoring the original source of the neoplastic cells or whether the presence of metastases or other forms of spreading of the neoplasia from the point of origin is to be monitored. In this regard, it may be desirable to harvest and test a number of different samples from any one organism. In another example, to the extent that one may be screening for the normal expansion of a lymphocyte clone, one would preferentially harvest a biological sample from a secondary lymphoid organ or, if the immune response has advanced such that an expanded clonal population has been released into the circulation, one may take a sample of blood or lymph fluid.

The method of the present invention provides a simple, efficient and accurate means of analysing a clonal population of cells based on the identification of the specific form of sequences which flank the marker region, to the extent that those flanking sequences correspond to genes or regions of genes which belong to a defined family of such genes. In this regard, reference to "analysing" should be understood in its broadest sense and includes, but is not limited to, the characterisation, detection, isolation, amplification or quantification of the marker sequence. The analysis of these flanking sequences in accordance with this method now facilitates a range of potential applications including, but not limited to:

(i) a means of enriching a nucleic acid population, derived from a biological sample, for the nucleic acid material which is flanked by the flanking sequences identified hereby. Such enrichment methodology is particularly useful where a biological sample comprises a highly heterogeneous mix of cell types.

Reference to "enriching" should be understood as a reference to increasing the ratio of nucleic acid molecules expressing the marker nucleic acid region relative to the background non-marker nucleic acid molecules contained in a test sample. Enrichment can be achieved, for example, by degrading, removing or otherwise reducing nucleic acid molecules which do not express the specific flanking sequence combination identified hereby. By providing for an enrichment step which can be designed to decrease the non-relevant nucleic acid molecules from the test sample, rather than necessarily amplifying the nucleic acid population of interest, the subject detection method provides a highly sensitive tool which is not compromised by the risk of non-specific amplification occurring. It should be understood that reference to "enrichment" is not limited to an enrichment step which removes all non-relevant nucleic acid molecules from the test sample. Rather, it is a reference to decreasing the concentration of irrelevant nucleic acid molecules in a test sample. This concentration may therefore be of varying degrees.

Enriching for nucleic acid molecules comprising the marker sequence can be performed by any one or more of a number of suitable techniques including, but not limited to, incorporating a tag into a probe molecule which is directed to the flanking sequences which have been identified in accordance with the method of the present invention. The tag can be used to couple molecules to a solid phase whether by covalent bond or by non-covalent bonds in order to facilitate removal of unwanted molecules by washing or other means. Enrichment can also be performed alternatively, or in addition to any initial enrichment step, by performing a nucleic acid amplification technique which utilises primers directed towards one or both flanking sequences.

(ii) Providing a means of monitoring the progression of a clonal population of cells in a subject. This is most likely to occur in the context of monitoring a patient in terms of the progression of a disease state or non-disease state which is characterised by the clonal expansion of a population of cells. For example, there is significant potential for the application of the method of the present invention in terms of patients suffering from malignant and non-malignant neoplasia. However, there may also be potential to apply the present invention in the context of patients suffering various forms of immunodeficiency, where one may seek to screen for the nature of specific immune cell expansion which can be mounted by that individual's immune system. Such monitoring may be performed via the enrichment methodology described in point (i), above, for example.

(iii) The flanking sequences which are identified in accordance with the method of the present invention provide a simple and efficient means of marking a population of cells. For example, once these sequences have been identified, one can routinely screen populations of cells in order to identify (either qualitative and/or quantitatively) the existence of the population of cells expressing that specific marker. This may be performed in the absence of any subsequent enrichment step. The identification of unique mutations expressed by a clonal population of cells, such as a neoplastic clone, can be highly complex and difficult to achieve, however the method of the present invention provides a relatively routine means of characterising a clonal cell population, thereby providing a marker for ongoing detection/monitoring applications without the need to conduct elaborate genetic analyses.

(iv) The method facilitates detection of a clonal population of cells when use of "consensus" primers has been unable to achieve this. By attempting nucleic acid amplification on a test sample using individual primers directed towards an individual member of each family of sequences, and using the primers either singly or in multiplexes, one may successfully demonstrate the presence of a clonal population and, by identifying it and determining the flanking sequences, one may enable subsequent monitoring of that population.

(v) When multiple malignant clones are present in a malignant population, by use of a large number of nucleic acid amplification reactions, each of which uses a different pair of primers and such that the totality of use of different primers covers the total combination of primers directed towards individual members of the two flanking families, and by performing nucleic acid amplification in a quantitative fashion, one may measure the relative sizes of the various malignant subclones. This may be of value in many situations including, but not limited to, following malignant clones in a patient with lymphoid cancer.

(vi) When multiple clones are present in a population, such as normal immune clones in a polyclonal population, by use of a large number of nucleic acid amplification reactions, each of which uses a different pair of primers and such that the totality of use of different primers covers the total combination of primers directed towards individual members of the two flanking families, and by performing nucleic acid amplification in a quantitative fashion, one may measure the relative sizes of the various clones. This may be of value in many situations including, but not limited to, study of the immune system under conditions of normal physiology or abnormal pathology.

Accordingly, in another aspect there is provided a method of diagnosing and/or monitoring a clonal population of cells in a mammal, which clonal cells are characterised by a marker nucleic acid molecule and which marker nucleic molecule is flanked by sequences which are members of a family of distinct repeated sequences identified in accordance with the methods hereinbefore described, said method comprising screening the nucleic acid molecules of a biological sample from said mammal for the presence of said flanking sequences. Preferably, said clonal population of cells is a neoplastic population of cells, an immune population of cells or a microorganism population. Still more preferably, said immune population is a T cell population or a B cell population.

With respect to this aspect of the present invention, reference to "monitoring" should be understood as a reference to testing the subject for the presence or level of the subject clonal population of cells after initial diagnosis of the existence of said population. "Monitoring" includes reference to conducting both isolated one off tests or a series of tests over a period of days, weeks, months or years. The tests may be conducted for any number of reasons including, but not limited to, predicting the likelihood that a mammal which is in remission will relapse, monitoring the effectiveness of a treatment protocol, checking the status of a patient who is in remission, monitoring the progress of a condition prior to or subsequently to the application of a treatment regime, in order to assist in reaching a decision with respect to suitable treatment or in order to test new forms of treatment. The method of the present invention is therefore useful as both a clinical tool and a research tool.

In yet another aspect there is provided a method of diagnosing and/or monitoring a mammalian disease condition characterised by a clonal population of cells, which clonal cells are characterised by a marker nucleic acid molecule and which marker nucleic molecule is flanked on one or both sides by sequences which are members of a family of distinct repeated sequences identified in accordance with the methods of any one of claims 1-15, said method comprising screening the nucleic acid molecules of a biological sample from said mammal for the presence of said flanking sequences.

Preferably, said clonal population of cells is a neoplastic population of cells, an immune population of cells or a microorganism population. Still more preferably, said immune cell population is a T cell population or a B cell population.

Most preferably, said population of cells is a neoplastic population of cells and said condition is a malignant or a non-malignant neoplastic condition.

In another most preferred embodiment, said population of cells is an immune cell population and said condition is a wanted or unwanted immune response or an immunodeficiency condition such as AIDS.

In still yet another preferred embodiment, said clonal population is a microorganism population and said condition is an infection.

In accordance with those preferred aspect of the present invention, to the extent that said clonal population is a T or B cell population, said marker nucleic acid region is preferably a rearranged immunoglobulin or T cell receptor variable region gene segment and said distinct repeated sequence is a V, D or J gene segment.

Yet another aspect of the present invention is directed to a method of enriching for a population of nucleic acid molecules in a biological sample, which nucleic acid molecules are characterised by a marker nucleic acid molecule and which marker nucleic acid molecule is flanked on one or both sides by sequences which are members of a family of distinct repeated sequences identified in accordance with the methods of any one of claims 1-15, said method comprising increasing the ratio of nucleic acid molecules comprising said flanking sequence relative to nucleic acid molecules which do not comprise said flanking sequence.

Further features of the present invention are more fully described in the following non-limiting Examples.

EXAMPLE 1

Schematic Flow Chart to Illustrate Quantification of Leukaemia During Treatment

Starting material—polyclonal population of lymphocytes, containing clones of various sizes ranging from 1 to very many cells
  each clone characterised by 1 of >50 V segments, 1 of >30 D segments and 1 of 6 J segments
  leukaemic clone for analysis has unknown V, D and J segments (say for argument $V_{23}$, $D_7$ and $J_4$)
Using leukaemic cells at diagnosis as a relatively pure clonal population
  determine flanking J, V and D segments ($J_4$, $V_{23}$ and $D_7$ in this case).
Analyse above starting material
  Amplification reaction on starting material with $V_{23}$ and $J_4$ primers↓
  Amplification reaction on $V_{23}$ and $J_4$ amplified material with $D_7$ and $J_4$ primers↓
  Amplified material is largely or wholly derived from only those clones characterised by $V_{23}$, $D_7$ and $J_4$. It is thus greatly enriched for material derived from the leukaemic clone.↓
  Analyse marker region of amplified material by quantitative polymerase chain reaction and/or by studying length and/or sequence using methods such as electrophoresis or chromatography in order to detect and/or quantify the leukaemic clone in the starting material.

Schematic Flow Chart to Illustrate Quantification of Multiple Clones when Flanking Sequences are not Already Known
  Set up multiple amplification reactions from material being studied, each using a different pair of primers (usually one V and one J for each pair, but could also be one V and one D, or one D and one J)↓
  Analyse marker region of amplified material of each reaction showing amplification by quantitative polymerase chain reaction and/or by studying length and/or sequence using methods such as electrophoresis or chromatography or by further multiple amplification reactions using different primer pairs

EXAMPLE 2

Protocol for Identifying J, V, D Regions

J Screen
  taqman probe MJB2
  use 10 ng diagnostic DNA per tube with each tube in duplicate
  3A-J1, J1dup, J2, J2dup, . . . J6, J6dup
  28 tubes including controls
  perform quantitative PCR using file 92C for 15 seconds, 58C for 1 minute×45 cycles
  run relevant tracks on gel to verify size
  A Ct around 27-35 cycles indicates the J region for a dominant clone
Once have identified specific Jregion do V screen
V Screen
  taqman probe MJB2
  use 10 ng diagnostic DNA per tube with each tube in duplicate
  Vspecific (41 primers)-Jspecific
  90 tubes including controls
  perform quantitative PCR using file 92C for 15 seconds, 58C for 1 minute×45 cycles
  run relevant tracks on gel to verify size
  A Ct around 25-30 cycles indicates the V region for a dominant clone
D Screen
  taqman probe MJB2
  use dilution of approx. $1/100,000$ from Vspecific-Jspecific in V screen as template
  Dspecific (31 primers)-Jspecific
  65 tubes including controls
  perform quantitative PCR using file 40C×2 cycles (92 for 15 secs, 40C for 1 min)
  44C×2
  48C×2
  52C×2
  54C×2
  58C×30
  run relevant tracks on gel to verify size
  A Ct around 20-25 cycles indicates the D region for a dominant clone

EXAMPLE 3

Quantification of Leukaemia Using Primers Binding to Flanking Sequences

Results of quantification of leukaemia using primers binding to the flanking sequences, as shown schematically in Example 1, and with the flanking sequences and primers being identified by the protocol shown in Example 2. Leukaemic cells were mixed in known proportion with normal blood cells and the proportion of leukaemic cells in the mixture was then quantified using the Method. Each symbol shows the result from a different sample mixture. Note the close concordance between the "true" result, as inferred from the proportions in which the cells were mixed, and the measurement obtained by the Method.

Primers Currently in Use to Determine Flanking Sequences

V_H Primers Specific for Individual Vh Segments

| Vh family | Vh region | Location | Sequence 5' to 3' | SEQ ID NO: |
|---|---|---|---|---|
| 1 | 2 | CDR2 | ATCAACCCTAACAGTGGTGG | 1 |
| 1 | 3 | CDR2 | GCTGGCAATGGTAACACAAAA | 2 |
| 1 | 8 | CDR2 | ACCTAACAGTGGTAACACAGG | 3 |
| 1 | 18 | CDR2 | GGGATGGATCAGCGCTT | 4 |
| 1 | 24 | CDR2 | TGGAGGTTTTGATCCTGAAGA | 5 |
| 1 | 45 | CDR2 | ACACCTTTCAATGGTAACACC | 6 |
| 1 | 46 | CDR2 | GGGAATAATCAACCCTAGTGG | 7 |
| 1 | 58 | CDR2 | GATAGGATGGATCGTCGTTG | 8 |
| 1 | 69 | CDR2 | TCATCCCTATCTTTGGTACAG | 9 |
| 1 | C | — | [SEE PSEUDOGENE TABLE] | |
| 1 | E | — | USE 1.69, CDR2 | |
| 1 | F | — | USE 1.24, CDR2 | |
| 2 | 5 | CDR2 | ACTCATTTATTGGAATGATGATAAG | 10 |
| 2 | 5 var | CDR2 | ACTCATTTATTGGGATGATGATAAG | 11 |
| 2 | 26 | CDR2 | ACACATTTTTTCGAATGACGAA | 12 |
| 2 | 70 | CDR2 | TGATTGGGATGATGATAAATTCT | 13 |
| 3 | 7 | CDR2 | AGCAAGATGGAAGTGAGAAA | 14 |
| 3 | 9 | CDR2 | GGAATAGTGGTAGCATAGGC | 15 |
| 3 | 9B | CDR2 | TTGGAATAGTGGTAGCATAGG | 16 |
| 3 | 11 | CDR2 | CATTAGTAGTAGTGGTAGTACCAT | 17 |
| 3 | 11 | L-V intron | GAACTAGAGACATTGAGTGGA | 18 |
| 3 | 13 | CDR2 | TGGTACTGCTGGTGACACA | 19 |
| 3 | 13A | CDR2 | TCTCAGCTATTGGTACTGC | 20 |
| 3 | 15 | CDR2 | GCGGTATTAAAAGCAAAACTG | 21 |
| 3 | 16 | — | [SEE PSEUDOGENE TABLE] | |
| 3 | 19 | — | [USE V3-16, SEE PSEUD. TABLE] | |
| 3 | 20 | CDR2 | [GAATGGTGGTAGCACAGGT] | 22 |
| 3 | 20B | CDR2 | GCTGGAGTGGGTCTCT | 23 |
| 3 | 21 | CDR2 | CATCCATTAGTAGTAGTAGTT | 24 |
| 3 | 23 | CDR2 | GTGGGTCTCAGCTATTAGTG | 25 |
| 3 | 30 | CDR2 | AGTGGGTGGCAGTTATATCA | 26 |

-continued

| Vh family | Vh region | Location | Sequence 5' to 3' | SEQ ID NO: |
|---|---|---|---|---|
| 3 | 30.3 | | USE 3.64, CDR1 | |
| 3 | 30.5 | | USE 3.30, CDR2. | |
| 3 | 33 | CDR2 | AGTGGGTGGCAGTTATATGG | 27 |
| 3 | 35 | — | [USE V3-16, SEE PSEUD. TABLE] | |
| 3 | 38 | — | USE 3D, CDR2 | |
| 3 | 43 | CDR2 | GGTCTCTCTTATTAGTTGGGA | 28 |
| 3 | 47 | — | [SEE PSEUDOGENE TABLE] | |
| 3 | 48 | | USE 3.11, CDR2 [BUT NONSPECIFIC 3.48 PRIMER WAS ORDERED] | |
| 3 | 49 | CDR2 | ATGGTGGGACAACAGAATACA | 29 |
| 3 | 53 | CDR2 | GTGGGTCTCAGTTATTTATAGC | 30 |
| 3 | 53 | FR1 | AGCTGGTGGAGACTGGA | 31 |
| 3 | 64 | CDR2 | CTCAGCTATTAGTAGTAATGGG | 32 |
| 3 | 66 | — | USE 3.53, CDR2 | |
| 3 | 72 | CDR2 | AAACAAAGCTAACAGTTACACC | 33 |
| 3 | 73 | CDR2 | AAGCAAAGCTAACAGTTACG | 34 |
| 3 | 74 | CDR2 | TCACGTATTAATAGTGATGGGA | 35 |
| 3 | D | CDR2 | TCCATTAGTGGTGGTAGCA | 36 |
| 3 | H | — | [SEE PSEUDOGEN TABLE] | |
| 4 | 4 | CDR1 | CCATCAGCAGTAGTAACTGG | 37 |
| 4 | 4 | FR3 top | GTGGATTGGGCGTATCTATAC | 38 |
| 4 | 4B | | TAG TAA CTG GTG GAG TTG GG | 39 |
| 4 | 28 | CDR1 | USE 4.4, CDR1 | |
| 4 | 28 | FR1 | [TGCGCTGTCTCTGGTTA] | 40 |
| 4 | 28B | Codon 39 | GCAGTAGTAACTGGTGGG | 41 |
| 4 | 28C | Codon 97 | GCTCTGTGACCGCCGT | 42 |
| 4 | 28D | | SAME AS 28C | |
| 4 | 30.1 | FR1 | GACTGGTGAAGCCTTCACA | 43 |
| 4 | 30.2 | — | USE 4.30.1, FR1 | |
| 4 | 30.2B | Codon 9.1 | TGC AGG AGT CCG GCT | 44 |
| 4 | 30.4 | — | USE 4.30.1, FR1 | |
| 4 | 31 | — | USE 4.30.1, FR1 | |
| 4 | 31b | Codon 83.3 | ACC ATA TCA GTA GAC ACG TCT | 45 |
| 4 | 34 | FR1 | TATGGTGGGTCCTTCAGTG | 46 |

-continued

| Vh family | Vh region | Location | Sequence 5' to 3' | SEQ ID NO: |
|---|---|---|---|---|
| 4 | 34B | | SAME AS 4.34 | |
| 4 | 39 | LV intron | AGGGCTCACTGTGGGTTTT | 47 |
| 4 | 39B | Codon 79.3 | AGA GTC GAG TCA CCA TAT CC | 48 |
| 4 | 59 | LV intron | CAGCTCCCAGATGTGAGTA | 49 |
| 4 | 59B | LV intron | SAME AS 4.59 | |
| 4 | 61 | FR1 | GTCTCTGGTGGCTCCG | 50 |
| 4 | 61B | | SAME AS 4.61 | |
| 4 | B | — | USE 4.28, FR1 | |
| 5 | 51 | CDR2 | CTGGTGACTCTGATACCAGA | 51 |
| 5 | 78 | — | USE 5-5 PRIMER, CDR2 | |
| 5 | A | CDR2 | ATCCTAGTGACTCTTATACCAAC | 52 |
| 6 | 1 | CDR2 | CATACTACAGGTCCAAGTGG | 53 |
| 7 | 4.1 | CDR2 | GATCAACACCAACACTGGG | 54 |
| 7 | 81 | — | USE 7-4.1 CDR2 PRIMER | |

J$_H$ Specific Primers

| J | Location down from ELJH | Sequence 5' to 3' | SEQ ID NO: |
|---|---|---|---|
| 1 | 60 bp | TCCCCAAGTCTGAAGCCA | 55 |
| 1c | 23 | ACA TGG CTC CCC GCT | 56 |
| 2 | 9 bp | GGAGGGGGCTGCAGTG | 57 |
| 2c | 34 | GGC TGG TGC TGG ACA G | 58 |
| [3] | 12 bp | AGAAAGGAGGCAGAAGGAA | 59 |
| 3B 2002 | 46 | CCCAGCTCCAGGACAGA | 60 |
| 3c | | GAA AGG AGG CAG AAG GAA A | 61 |
| [4 2002] | 18 bp | TCGAGTTAACGGAGGAGA | 62 |
| [4A 2002] | 23 bp | AAACCTCGAGTTAACGGAG | 63 |
| [4B 2002] | 36 bp | AAATGCAGCAAAACCCTTC | 64 |
| 4C 2002 | 83/78/73 bp | GGGGCTCTCTTGGCAGG | 65 |
| 4d 2003 | 86/81/76 bp | TCC GGG GCT CTC TTG G | 66 |
| 4 IVS | 82/78/73 bp | TGCTCCGGGGCTCTCTTGGCAGGA | 67 |
| 4e | 19/20 | GAG TTA AAG GAG GAG A | 68 |
| 4f | 58/63/65 | CCC CCA GCA CCC TTA TT | 69 |
| 5 | 35 bp | GCAAGCTGAGTCTCCCT | 70 |
| 5c | 24 | GTC TCC CTA AGT GGA CTC A | 71 |
| 6 | 10 bp | ACAAAGGCCCTAGAGTGG | 72 |
| 6c | 35 | AAA CCC CAC AGG CAG TAG | 73 |
| 1 dup | 83 | CGACCTCCTTTGCTGAG | 74 |
| 2 dup | 79 | GGCTGCAGACCCCAGA | 75 |
| 3 dup | 80 | CAGCGCAGACCAAGGA | 76 |
| 4 dup | Ca. 145 | TTGCCCCTCGTCTGTGT | 77 |
| 5 dup | 84 | CTTTCTTTCCTGACCTCCAA | 78 |
| 6 dup | 31 bp | CCCACAGGCAGTAGCAG | 79 |

D$_H$ Primers for V-D-J Rearrangements

| IgH Diversity | Basic sequence | SEQ ID NO: | Edited sequence | SEQ ID NO: |
|---|---|---|---|---|
| D1.1 std | Ggtacaact | 80 | aacgacggccagtGgtacaact | 129 |
| D1.1 longer | ggtacaactgga | 81 | aacgacggccagtggtacaactgga | 130 |
| D1.07 std | Ggataactggaact | 82 | aacgacggccagtGgtataactggaact | 131 |
| D1.07 shorter | Ggtataactgga | 83 | aacgacggccagtGgtataactgga | 132 |
| D1.14 std | Ggtataacc | 84 | aacgacggccagtGgtataacc | 133 |
| D1.14 longer | Ggtataaccgga | 85 | aacgacggccagtGgtataaccgga | 134 |
| D1.20 std | ggTataactggaacg | 86 | aacgacggccagtggTataactggaacg | 135 |
| D1.20 shorter | -use 1.7 shorter | | -use 1.7 shorter | |
| D1.26 std | Ggtatagtgggag | 87 | aacgacggccagtGgtatagtgggag | 136 |
| D1.26 longer | Ggtatagtgggagctac | 88 | aacgacggccagtGgtatagtgggagctac | 137 |
| D2.02 std | Aggatattgtagtagtaccagc | 89 | aacgacggccagtAggatattgtagtagtaccagc | 138 |
| D2.02 shorter | Aggatattgtagtagtacc | 90 | aacgacggccagtAggatattgtagtagtacc | 139 |
| D2.08 std | Aggatattgtactaatggtgta | 91 | aacgacggccagtAggatattgtactaatggtgta | 140 |
| D2.08 longer | Aggatattgtactaatggtgtatgc | 92 | aacgacggccagtgatattgtactaatggtgtatgc | 141 |
| D2.15 std | Aggatattgtagtggtggtagc | 93 | aacgacggccagtgatattgtagtggtggtagc | 142 |

-continued

| IgH Diversity | Basic sequence | SEQ ID NO: | Edited sequence | SEQ ID NO: |
|---|---|---|---|---|
| D2.15 longer | Aggatattgtaatggtggtagctg | 94 | aacgacggccagtAtatattgtagtggtggtagctg | 143 |
| D2.21 std | Agcatattgtggtg | 95 | aacgacggccagtAgctattgtggtg | 144 |
| D2.21 longer | Agcatattgtggtggtga | 96 | aacgacggccagtAgcatattgtggtggtga | 145 |
| D3.03 std | gTattacgattttgga | 97 | aacgacggccagtgTattacgattttttgga | 146 |
| D3.03 longer | gTattacgattttggagtg | 98 | aacgacggccagtgTattacgattttttggagtg | 147 |
| D3.09 std | Gtattacgatattttgac | 99 | aacgacggccagtGtattacgatattttgac | 148 |
| D3.09 longer | Gtattacgatattttgactg | 100 | aacgacggccagtGtattacgatattttgactg | 149 |
| D3.10 std | Gtattactatggttcgggga | 101 | aacgacggccagtGtattactatggttcgggga | 150 |
| D3.10 shorter | Gtattactatggttc | 102 | aacgacggccagtGtattactatggttc | 151 |
| D3.16 std | gTtatgattacgtttggg | 103 | aacgacggccagtgTtatgattacgtttggg | 152 |
| D3.16 longer | gTtatgattacgtttgggga | 104 | aacgacggccagtgTtatgattacgtttgggga | 153 |
| D3.22 std | Gtattactatgatag | 105 | aacgacggccagtGtattactatgatag | 154 |
| D3.22 longer | Gtattactatgatagtagtg | 106 | aacgacggccagtGtattactatgatagtagtg | 155 |
| D4.04 & D4.11 std | Tgactacagta | 107 | aacgacggccagtTgactacagta | 156 |
| D4.04 & D4.11 longer | Tgactacagtaac | 108 | aacgacggccagtTgacacagtaac | 157 |
| D4.17 std | Tgactacggtg | 109 | aacgacggccagtTgactacggtg | 158 |
| D4.17 longer | Tgactacggtgact | 110 | aacgacggccagtTgactacggtgact | 159 |
| D4.23 std | Tgactacggtggt | 111 | aacgacggccagtTgactacggtggt | 160 |
| D4.23 longer | Tgactacggtggtta | 112 | aacgacggccagtTgactacggtggtta | 161 |
| D5.05 & D5.18 std | Gtggataca | 113 | aacgacggccagtGtggataca | 162 |
| D5.05 & D5.18 longer | Gtggatacagct | 114 | aacgacggccagtGtggatacagct | 163 |
| D5.12 std | Gtggatatagtggctac | 115 | aacgacggccagtGtggatatagtggctac | 164 |
| D5.12 longer | Gtggatatagtggctacgat | 116 | aacgacggccagtGtggatatagtggctacgat | 165 |
| D5.24 std | Gtagagatg | 117 | aacgacggccagtGtagagatg | 166 |
| D5.24 longer | Gtagagatggctaca | 118 | aacgacggccagtGtagagatggctaca | 167 |
| D6.06 std | Gagtatagcagct | 119 | aacgacggccagtGagtatagcagct | 168 |
| D6.06 longer | Gagtatagcagctgct | 120 | aacgacggccagtGagtatagcagctgct | 169 |
| D6.13 std | Gggtatagcagca | 121 | aacgacggccagtGggtatagcagca | 170 |
| D6.13 longer | Gggtatagcagcagctg | 122 | aacgacggccagtGggtatagcagcagctg | 171 |
| D6.19 std | Gggtatagcagtgg | 123 | aacgacggccagtGggtatagcagtgg | 172 |
| D6.19 longer | Gggtatagcagtggctgg | 124 | aacgacggccagtggtatagcagtggctgg | 173 |
| D6.25 std | Gggtatagcagcgg | 125 | aacgacggccagtGggtatagcagcgg | 174 |
| D7.27 std | Ctaactgg | 126 | aacgacggccagtCtaactgg | 175 |
| D7.27 | Ctaactgggg | 127 | aacgacggccagtCtaactgggg | 176 |
| 13 base USP adaptor | aacgacggccagt | 128 | | |

TCR Beta Primers Specific for Individual V Segments

| TCR V family-segment* allele | Primer sequences, corrected to Tm of 50 celsius | Primer location | SEQ ID NO |
|---|---|---|---|
| 1 * | AGA CAG AAA GCT AAG AAA TCC | CDR2 49.3 | 177 |
| 2 | CA AAT CTT GGG GCA GAA AG | CDR2 50.1 | 178 |
| 3-1 | TA AGA AAT TTC TGA AGA TAA TGT TTA G | CDR2 55.2 | 179 |
| 3-2 * | TC TAC AGT AAC AAG GAG CCA | CDR2 61.3 | 180 |
| 4-1 | CT ATG AGA AAC TCT CTA TAA ATG AA | CDR2 69.3 | 181 |
| 4-2 | TGT CTA CAA CTT TAA AGA ACA GAC | CDR2 66.2 | 182 |
| 4-3 | TAC AGT CTT GAA GAA CGG GT | CDR2 66.2 | 183 |

-continued

| TCR V family-segment* allele | Primer sequences, corrected to Tm of 50 celsius | Primer location | SEQ ID NO |
|---|---|---|---|
| 5-1 | TTT GAA TAC TTC AGT GAG ACA C | CDR2 61.1 | 184 |
| 5-3 | GCT AAT GAG TTA AGG AGA TCA G | CDR2 68.1 | 185 |
| 5-4 | AGT ATT ATA GGG AGG AAG AGA AT | CDR2 66.3 dimer, but try it anyway | 186 |
| 5-5/5-7 | TAT GAG AAA GAA GAG AGA GGA | CDR2 67.3 | 187 |
| 5-6 | TGA GGA GGA AGA GAG ACA G | CDR2 67.3 | 188 |
| 5-7 | Use 5-5 | No unique bases in coding seq | |
| 5-8 | CCT TTG GTA TGA CGA GGG T | CDR2 59.1 | 189 |
| 6-1 | GCT GAT TTA TTA CTC AGC TTC | CDR2 58.2 | 190 |
| 6-2/6-3 | ACT CAG TTG GTG AGG GTA CA | CDR2 61.3 | 191 |
| 6-3 | Use 6-2 | — | |
| 6-4 | AGA TGT ACC CAG GAT ATG AGA | CDR2 28.3 | 192 |
| 6-5 | GGT GCT GGT ATC ACT GAC C | CDR2 68.1 | 193 |
| 6-6 | GAG GCA TGG CCC TGA A | CDR2 51.2 ?5 loci | 194 |
| 6-7 | GAG TTG CTG CTG CTC T | CDR2 61.2 | 195 |
| 6-8 | GCT GGT ACT ACT GAG AAA GA | CDR2 70.2 | 196 |
| 6-9 | ATG GGG CTG AGG CGC | CDR2 52.3 ?redesign | 197 |
| 7-1 | AAT TTA CTT CCA AGG CAA GGA | CDR2 60.2 | 198 |
| 7-2 | TAA TTT ACT TCC AAG GCA ACA G | CDR2 60.2 | 199 |
| 7-3 | GGG TGC GGC AGA TGA C | CDR2 68.3 | 200 |
| 7-4 | TGA CTT ACT CCC AGA GTG AT | CDR2 59.3 dimer, but try it. | 201 |
| 7-5 * | GCT CAG TGA TCA ATT CTC CA | CDR2 78.1 ?2 loci | 202 |
| 7-6/7-7 | CTT CAA TTA TGA AGC CCA ACA | CDR2 66.2 | 203 |
| 7-7 | Use 7-6 | Only 1 base unique to 7.7 codon 26 position 1 | |
| 7-8 | GAT CGC TTC TTT GCA GAA | CDR2 79.3 ?2 loci | 204 |
| 7-9 | GAA GCT CAA CTA GAA AAA TCA A | CDR2 70.1;3' mismatch, 1 of 4 | 205 |
| 9 | CGA TTC TCC GCA CAA CA | CDR2 80.2 | 206 |
| 10-1 | ATT ACT CAT ATG GTG TTC ACG AC | CDR2 61.3;-4 mismatch, 1 Of 3 | 207 |
| 10-2 | TCA GCA GCT GCT GAT ATT | CDR2 61.3 | 208 |
| 10-3 | GAG AGA GAC ACC AAC ACC A | CDR1 18.3 | 209 |
| 11-1 | GTT CAA TTT GAG GAT GAG AGT | CDR2 60.3 | 210 |
| 11-2 | GAT TCA GTT TCA GAA TAA CGG T | CDR2 60.3 | 211 |

-continued

| TCR V family-segment* allele | Primer sequences, corrected to Tm of 50 celsius | Primer location | SEQ ID NO |
|---|---|---|---|
| 11-3 | GAT TCG ATA TGA AAA TGA GGA A | CDR2 60.3 | 212 |
| 12-1 * | CTG GAG CTG GAG CCT C | CDR2 61.3 | 213 |
| 12-2 * | GCA GGT ATG CCC ACA GAG | Cdr2 74.3 | 214 |
| 12-3 | CCA ATT TCA GGC CAC AAC TC | CDR1 31.2 | 215 |
| 12-4 | CCA ATT TCA GGA CAC GAC TA | CDR1 31.2 dimer - try it anyway | 216 |
| 12-5 | TAC TTC CGC AAC CGG G | CDR2 60.1 | 217 |
| 13 | CTC ATT TCG TTT TAT GAA AAG ATG | CDR2 60.3 | 218 |
| 14 | TGT TAC ATT TTG TGA AAG AGT CT | CDR2 60.3 | 219 |
| 15 | CCC TGA TAA CTT CCA ATC CAG | CDR2 79.2 | 220 |
| 16 | AGG TCC TGA AAA ACG ACT TC | CDR2 50.3 | 221 |
| 17 | CCT TCC AGT ACC AAA ACA TTG | CDR2 66.1 | 222 |
| 18 | AAG GTC TGA AAT TCA TGG TTT ATC | CDR2 56.1 | 223 |
| 19 | TGA CTT TCA GAA AGG AGA TAT AG | CDR2 72.1 | 224 |
| 20-1 | GGG CTC CAA GGC CAC A | CDR2 68.3 | 225 |
| 21-1 * | AGA AAG CAG AAA TAA TCA ATG AG | CDR2 74.3 | 226 |
| 23-1 | TTT TGA TTT CCT TTC AGA ATG AAC | CDR2 60.1 | 227 |
| 24-1 | TTG ATC TAT TAC TCC TTT GAT GTC | CDR2 59.3 | 228 |
| 25-1 | GAG ATC TTT CCT CTG AGT CA | CDR2 76.3 | 229 |
| 26 * | CAC CTG GCA CTG GGA G | CDR2 61.2 | 230 |
| 27 | GGC TGG GCT TAA GGC A | CDR2 52.2 | 231 |
| 28 | ATC TAT TTC TCA TAT GAT GTT AAA ATG | CDR2 61.3 | 232 |
| 29-1 | TGA CAC TGA TCG CAA CTG | CDR2 56.1 | 233 |
| 30 | ACA GGC TGC AGG CAG | CDR2 48.2, T2 loci, allele 30-03 won't bind | 234 |

* de-listed on IMGT repertoire, 3 Apr. 2003

TCR Beta J Segment Specific Primers

| J beta segment | Distance to end of J | primer | SEQ ID NO |
|---|---|---|---|
| J1.1 | | TTT TCC CTG TGA CGG ATG T | 235 |
| J1.2 | | CAG GAC AGA GTC CTC CCT | 236 |
| J1.3 | | AGC CCC TTT TTG CAA GTT C | 237 |
| J1.4 | | AAC TCC GAC CTT ATG ATA CAC T | 238 |
| J1.5 | | TGC CTT CAA GGG ACA ATG G | 239 |
| J1.6 | | GAT CAT TGC AGT CAA ACC | 240 |
| J2.1 | | GGC TGG GCT GCT CAC | 241 |
| J2.2 | | ATC CGC CCC TCT CGG | 242 |
| J2.3 | | CAG TTC GGG GGC TTC AG | 243 |
| J2.4 | | GAG CGC AGT CTC GTC C | 244 |
| J2.5 | | CGC AAA AAC CAG ACC CAA | 245 |
| J2.6 | | CCG CCT TCC ACC TGA A | 246 |
| J2.7 | | GGG ACC GAG GGG CTG | 247 |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. A method of analysing a rearranged immunoglobulin or T cell receptor variable region gene, the rearranged gene being characteristic of a clonal population of cells, said method comprising identifying one or more of the V, D or J gene segments of said rearranged gene utilizing an amplification primer or hybridization probe that is specific to an individual gene segment.

2. The method according to claim 1 wherein said rearranged immunoglobulin or T cell receptor variable region gene nucleic acid is DNA.

3. The method according to claim 2 wherein said clonal population of cells is an immune cell population.

4. The method according to claim 3 wherein said clonal population of immune cells is a neoplastic population of cells.

5. The method according to claim 3 wherein said immune cell population is a T cell population.

6. The method according to claim 3 wherein said immune cell population is a B cell population.

7. The method according to claim 3 wherein the gene segments which are identified are the V and D gene segments.

8. The method according to claim 3 wherein the gene segments which are identified are the V and J gene segments.

9. The method according to claim 3 wherein the gene segments which are identified are the D and J gene segments.

10. The method according to any one of claims 1, 2, 3-6 and 7-9, wherein said identification method is an amplification reaction.

11. The method according to claim 10 wherein said identification method comprises:
    (i) performing a multiplicity of amplification reactions of nucleic acid molecules derived from said clonal cell population, each said amplification reaction utilising an upstream primer which is common to all reactions and is directed to a conserved region of the upstream gene segment and a downstream primer which is selected from a group of primers each of which is specific for a different individual downstream gene segment;
    (ii) identifying which of said downstream primers enables amplification of said downstream gene segment;
    (iii) repeating steps (i) and (ii) wherein said downstream primer is common to all reactions and is directed to a conserved region of the downstream gene segment and said upstream primer is selected from a group of primers each of which is specific for a different individual upstream gene segment.

12. The method according to claim 11 wherein said amplification reaction is a polymerase chain reaction.

13. The method according to claim 10 wherein said identification method comprises:
(i) performing a multiplicity of amplification reactions of nucleic acid molecules derived from said clonal cell population, each said amplification reaction utilising an upstream primer which is selected from a group of primers each of which is specific for a different individual upstream gene segment and a downstream primer which is selected from a group of primers each of which is specific for a different individual downstream gene segment; and
(ii) identifying which of said upstream and downstream primers enables amplification of said gene segments.

14. The method according to claim 13 wherein said amplification reaction is a polymerase chain reaction.

15. The method according to any one of claims 1, 2, 3-6 and 7-9 wherein said identification method comprises a nucleic acid hybridisation step, which comprises hybridisation reactions performed utilizing a microarray.

16. The method according to any one of claims 1, 2, 3-6 and 7-9 wherein said identification method comprises a nucleic acid sequencing step.

17. The method according to claim 16 wherein said nucleic acid sequencing is pyrosequencing.

18. The method according to claim 16 wherein said nucleic acid sequencing is minisequencing.

19. A method of detecting or monitoring a clonal population of cells in a mammal, which clonal cells are characterised by a rearranged immunoglobulin or T cell receptor variable region gene and which gene is analysed in accordance with the method of claim 1 to identify one or more of the V, D or J gene segments of said rearranged gene, said method comprising screening the nucleic acid molecules of a biological sample from said mammal for the presence of said V, D or J gene segment.

20. A method of diagnosing and/or monitoring a mammalian disease condition characterised by a clonal population of cells, which clonal cells are characterised by a rearranged immunoglobulin or T cell receptor variable region gene and which gene is analysed in accordance with the method of claim 1 to identify one or more of the V, D or J gene segments of said rearranged gene, said method comprising screening the nucleic acid molecules of a biological sample from said mammal for the presence of said V, D or J gene segment.

21. The method according to claim 19 or 20 wherein said clonal population of cells is an immune cell population.

22. The method according to claim 21 wherein said clonal population of immune cells is a neoplastic population of cells.

23. The method according to claim 21 wherein said immune cell population is a T cell population.

24. The method according to claim 21 wherein said immune cell population is a B cell population.

25. The method according to claim 21 wherein the gene segments which are identified are the V and D gene segments.

26. The method according to claim 21 wherein the gene segments which are identified are the V and J gene segments.

27. The method according to claim 21 wherein the gene segments which are identified are the D and J gene segments.

28. The method according to claim 20 wherein said condition is a neoplastic condition.

29. The method according to claim 28 wherein said neoplastic condition is a malignant neoplastic condition.

30. The method according to claim 28 wherein said neoplastic condition is a non-malignant neoplastic condition.

31. The method according to claim 20 wherein said condition is immunodeficiency and said screening is directed to detecting specific immune cell expansion.

32. The method according to claim 20 wherein said condition is an immune response and said screening is directed to detecting specific immune cell expansion.

33. A method of enriching for a population of nucleic acid molecules in a biological sample, which nucleic acid molecules are characterised by a rearranged immunoglobulin or T cell receptor variable region gene and which gene is analysed in accordance with the method of claim 1 to identify one or more of the V, D or J gene segments of said rearranged gene, said method comprising increasing the ratio of nucleic acid molecules comprising said V, D or J gene segments relative to nucleic acid molecules which do not comprise said V, D or J gene segments.

34. The method according to claim 33 wherein the gene segments which are identified are the V and D gene segments.

35. The method according to claim 33 wherein the gene segments which are identified are the V and J gene segments.

36. The method according to claim 33 wherein the gene segments which are identified are the D and J gene segments.

* * * * *

```
                          SEQUENCE LISTING

<160> NUMBER OF SEQ ID NOS: 247

<210> SEQ ID NO 1
<211> LENGTH: 20
<212> TYPE: DNA
<213> ORGANISM: Artificial Sequence
<220> FEATURE:
<223> OTHER INFORMATION: VH Primers

<400> SEQUENCE: 1
atcaacccta acagtggtgg                                                     20

<210> SEQ ID NO 2
<211> LENGTH: 21
<212> TYPE: DNA
<213> ORGANISM: Artificial Sequence
<220> FEATURE:
<223> OTHER INFORMATION: VH Primers

<400> SEQUENCE: 2
gctggcaatg gtaacacaaa a                                                   21

<210> SEQ ID NO 3
<211> LENGTH: 21
<212> TYPE: DNA
<213> ORGANISM: Artificial Sequence
<220> FEATURE:
<223> OTHER INFORMATION: VH Primers

<400> SEQUENCE: 3
acctaacagt ggtaacacag g                                                   21

<210> SEQ ID NO 4
<211> LENGTH: 17
<212> TYPE: DNA
<213> ORGANISM: Artificial Sequence
<220> FEATURE:
<223> OTHER INFORMATION: VH Primers

<400> SEQUENCE: 4
gggatggatc agcgctt                                                        17

<210> SEQ ID NO 5
<211> LENGTH: 21
<212> TYPE: DNA
<213> ORGANISM: Artificial Sequence
<220> FEATURE:
<223> OTHER INFORMATION: VH Primers

<400> SEQUENCE: 5
tggaggtttt gatcctgaag a                                                   21

<210> SEQ ID NO 6
<211> LENGTH: 21
<212> TYPE: DNA
<213> ORGANISM: Artificial Sequence
<220> FEATURE:
<223> OTHER INFORMATION: VH Primers

<400> SEQUENCE: 6
```

-continued acacctttca atggtaacac c                                        21

<210> SEQ ID NO 7
<211> LENGTH: 21
<212> TYPE: DNA
<213> ORGANISM: Artificial Sequence
<220> FEATURE:
<223> OTHER INFORMATION: VH Primers

<400> SEQUENCE: 7
gggaataatc aaccctagtg g                                        21

<210> SEQ ID NO 8
<211> LENGTH: 20
<212> TYPE: DNA
<213> ORGANISM: Artificial Sequence
<220> FEATURE:
<223> OTHER INFORMATION: VH Primers

<400> SEQUENCE: 8
gataggatgg atcgtcgttg                                          20

<210> SEQ ID NO 9
<211> LENGTH: 21
<212> TYPE: DNA
<213> ORGANISM: Artificial Sequence
<220> FEATURE:
<223> OTHER INFORMATION: VH Primers

<400> SEQUENCE: 9
tcatccctat ctttggtaca g                                        21

<210> SEQ ID NO 10
<211> LENGTH: 25
<212> TYPE: DNA
<213> ORGANISM: Artificial Sequence
<220> FEATURE:
<223> OTHER INFORMATION: VH Primers

<400> SEQUENCE: 10
actcatttat tggaatgatg ataag                                    25

<210> SEQ ID NO 11
<211> LENGTH: 25
<212> TYPE: DNA
<213> ORGANISM: Artificial Sequence
<220> FEATURE:
<223> OTHER INFORMATION: VH Primers

<400> SEQUENCE: 11
actcatttat tgggatgatg ataag                                    25

<210> SEQ ID NO 12
<211> LENGTH: 22
<212> TYPE: DNA
<213> ORGANISM: Artificial Sequence
<220> FEATURE:
<223> OTHER INFORMATION: VH Primers

<400> SEQUENCE: 12
acacattttt tcgaatgacg aa                                       22

<210> SEQ ID NO 13
<211> LENGTH: 23
<212> TYPE: DNA
<213> ORGANISM: Artificial Sequence

```
<220> FEATURE:
<223> OTHER INFORMATION: VH Primers

<400> SEQUENCE: 13
tgattgggat gatgataaat tct                                           23

<210> SEQ ID NO 14
<211> LENGTH: 20
<212> TYPE: DNA
<213> ORGANISM: Artificial Sequence
<220> FEATURE:
<223> OTHER INFORMATION: VH Primers

<400> SEQUENCE: 14
agcaagatgg aagtgagaaa                                               20

<210> SEQ ID NO 15
<211> LENGTH: 20
<212> TYPE: DNA
<213> ORGANISM: Artificial Sequence
<220> FEATURE:
<223> OTHER INFORMATION: VH Primers

<400> SEQUENCE: 15
ggaatagtgg tagcataggc                                               20

<210> SEQ ID NO 16
<211> LENGTH: 21
<212> TYPE: DNA
<213> ORGANISM: Artificial Sequence
<220> FEATURE:
<223> OTHER INFORMATION: VH Primers

<400> SEQUENCE: 16
ttggaatagt ggtagcatag g                                             21

<210> SEQ ID NO 17
<211> LENGTH: 24
<212> TYPE: DNA
<213> ORGANISM: Artificial Sequence
<220> FEATURE:
<223> OTHER INFORMATION: VH Primers

<400> SEQUENCE: 17
cattagtagt agtggtagta ccat                                          24

<210> SEQ ID NO 18
<211> LENGTH: 21
<212> TYPE: DNA
<213> ORGANISM: Artificial Sequence
<220> FEATURE:
<223> OTHER INFORMATION: VH Primers

<400> SEQUENCE: 18
gaactagaga cattgagtgg a                                             21

<210> SEQ ID NO 19
<211> LENGTH: 19
<212> TYPE: DNA
<213> ORGANISM: Artificial Sequence
<220> FEATURE:
<223> OTHER INFORMATION: VH Primers

<400> SEQUENCE: 19
tggtactgct ggtgacaca                                                19
```

```
<210> SEQ ID NO 20
<211> LENGTH: 19
<212> TYPE: DNA
<213> ORGANISM: Artificial Sequence
<220> FEATURE:
<223> OTHER INFORMATION: VH Primers

<400> SEQUENCE: 20
tctcagctat tggtactgc                                          19

<210> SEQ ID NO 21
<211> LENGTH: 21
<212> TYPE: DNA
<213> ORGANISM: Artificial Sequence
<220> FEATURE:
<223> OTHER INFORMATION: VH Primers

<400> SEQUENCE: 21
gcggtattaa aagcaaaact g                                       21

<210> SEQ ID NO 22
<211> LENGTH: 19
<212> TYPE: DNA
<213> ORGANISM: Artificial Sequence
<220> FEATURE:
<223> OTHER INFORMATION: VH Primers

<400> SEQUENCE: 22
gaatggtggt agcacaggt                                          19

<210> SEQ ID NO 23
<211> LENGTH: 16
<212> TYPE: DNA
<213> ORGANISM: Artificial Sequence
<220> FEATURE:
<223> OTHER INFORMATION: VH Primers

<400> SEQUENCE: 23
gctggagtgg gtctct                                             16

<210> SEQ ID NO 24
<211> LENGTH: 24
<212> TYPE: DNA
<213> ORGANISM: Artificial Sequence
<220> FEATURE:
<223> OTHER INFORMATION: VH Primers

<400> SEQUENCE: 24
catccattag tagtagtagt agtt                                    24

<210> SEQ ID NO 25
<211> LENGTH: 20
<212> TYPE: DNA
<213> ORGANISM: Artificial Sequence
<220> FEATURE:
<223> OTHER INFORMATION: VH Primers

<400> SEQUENCE: 25
gtgggtctca gctattagtg                                         20

<210> SEQ ID NO 26
<211> LENGTH: 20
<212> TYPE: DNA
<213> ORGANISM: Artificial Sequence
<220> FEATURE:
<223> OTHER INFORMATION: VH Primers
```

<400> SEQUENCE: 26
agtgggtggc agttatatca                                              20

<210> SEQ ID NO 27
<211> LENGTH: 20
<212> TYPE: DNA
<213> ORGANISM: Artificial Sequence
<220> FEATURE:
<223> OTHER INFORMATION: VH Primers

<400> SEQUENCE: 27
agtgggtggc agttatatgg                                              20

<210> SEQ ID NO 28
<211> LENGTH: 21
<212> TYPE: DNA
<213> ORGANISM: Artificial Sequence
<220> FEATURE:
<223> OTHER INFORMATION: VH Primers

<400> SEQUENCE: 28
ggtctctctt attagttggg a                                            21

<210> SEQ ID NO 29
<211> LENGTH: 21
<212> TYPE: DNA
<213> ORGANISM: Artificial Sequence
<220> FEATURE:
<223> OTHER INFORMATION: VH Primers

<400> SEQUENCE: 29
atggtgggac aacagaatac a                                            21

<210> SEQ ID NO 30
<211> LENGTH: 22
<212> TYPE: DNA
<213> ORGANISM: Artificial Sequence
<220> FEATURE:
<223> OTHER INFORMATION: VH Primers

<400> SEQUENCE: 30
gtgggtctca gttatttata gc                                           22

<210> SEQ ID NO 31
<211> LENGTH: 17
<212> TYPE: DNA
<213> ORGANISM: Artificial Sequence
<220> FEATURE:
<223> OTHER INFORMATION: VH Primers

<400> SEQUENCE: 31
agctggtgga gactgga                                                 17

<210> SEQ ID NO 32
<211> LENGTH: 22
<212> TYPE: DNA
<213> ORGANISM: Artificial Sequence
<220> FEATURE:
<223> OTHER INFORMATION: VH Primers

<400> SEQUENCE: 32
ctcagctatt agtagtaatg gg                                           22

<210> SEQ ID NO 33

```
<211> LENGTH: 22
<212> TYPE: DNA
<213> ORGANISM: Artificial Sequence
<220> FEATURE:
<223> OTHER INFORMATION: VH Primers

<400> SEQUENCE: 33
aaacaaagct aacagttaca cc                                              22

<210> SEQ ID NO 34
<211> LENGTH: 20
<212> TYPE: DNA
<213> ORGANISM: Artificial Sequence
<220> FEATURE:
<223> OTHER INFORMATION: VH Primers

<400> SEQUENCE: 34
aagcaaagct aacagttacg                                                 20

<210> SEQ ID NO 35
<211> LENGTH: 22
<212> TYPE: DNA
<213> ORGANISM: Artificial Sequence
<220> FEATURE:
<223> OTHER INFORMATION: VH Primers

<400> SEQUENCE: 35
tcacgtatta atagtgatgg ga                                              22

<210> SEQ ID NO 36
<211> LENGTH: 19
<212> TYPE: DNA
<213> ORGANISM: Artificial Sequence
<220> FEATURE:
<223> OTHER INFORMATION: VH Primers

<400> SEQUENCE: 36
tccattagtg gtggtagca                                                  19

<210> SEQ ID NO 37
<211> LENGTH: 20
<212> TYPE: DNA
<213> ORGANISM: Artificial Sequence
<220> FEATURE:
<223> OTHER INFORMATION: VH Primers

<400> SEQUENCE: 37
ccatcagcag tagtaactgg                                                 20

<210> SEQ ID NO 38
<211> LENGTH: 21
<212> TYPE: DNA
<213> ORGANISM: Artificial Sequence
<220> FEATURE:
<223> OTHER INFORMATION: VH Primers

<400> SEQUENCE: 38
gtggattggg cgtatctata c                                               21

<210> SEQ ID NO 39
<211> LENGTH: 20
<212> TYPE: DNA
<213> ORGANISM: Artificial Sequence
<220> FEATURE:
<223> OTHER INFORMATION: VH Primers

<400> SEQUENCE: 39
```

-continued

```
tagtaactgg tggagttggg                                              20

<210> SEQ ID NO 40
<211> LENGTH: 17
<212> TYPE: DNA
<213> ORGANISM: Artificial Sequence
<220> FEATURE:
<223> OTHER INFORMATION: VH Primers

<400> SEQUENCE: 40
tgcgctgtct ctggtta                                                 17

<210> SEQ ID NO 41
<211> LENGTH: 18
<212> TYPE: DNA
<213> ORGANISM: Artificial Sequence
<220> FEATURE:
<223> OTHER INFORMATION: VH Primers

<400> SEQUENCE: 41
gcagtagtaa ctggtggg                                                18

<210> SEQ ID NO 42
<211> LENGTH: 16
<212> TYPE: DNA
<213> ORGANISM: Artificial Sequence
<220> FEATURE:
<223> OTHER INFORMATION: VH Primers

<400> SEQUENCE: 42
gctctgtgac cgccgt                                                  16

<210> SEQ ID NO 43
<211> LENGTH: 19
<212> TYPE: DNA
<213> ORGANISM: Artificial Sequence
<220> FEATURE:
<223> OTHER INFORMATION: VH Primers

<400> SEQUENCE: 43
gactggtgaa gccttcaca                                               19

<210> SEQ ID NO 44
<211> LENGTH: 15
<212> TYPE: DNA
<213> ORGANISM: Artificial Sequence
<220> FEATURE:
<223> OTHER INFORMATION: VH Primers

<400> SEQUENCE: 44
tgcaggagtc cggct                                                   15

<210> SEQ ID NO 45
<211> LENGTH: 21
<212> TYPE: DNA
<213> ORGANISM: Artificial Sequence
<220> FEATURE:
<223> OTHER INFORMATION: VH Primers

<400> SEQUENCE: 45
accatatcag tagacacgtc t                                            21

<210> SEQ ID NO 46
<211> LENGTH: 19
<212> TYPE: DNA
```

<213> ORGANISM: Artificial Sequence
<220> FEATURE:
<223> OTHER INFORMATION: VH Primers

<400> SEQUENCE: 46
tatggtgggt ccttcagtg                                        19

<210> SEQ ID NO 47
<211> LENGTH: 19
<212> TYPE: DNA
<213> ORGANISM: Artificial Sequence
<220> FEATURE:
<223> OTHER INFORMATION: VH Primers

<400> SEQUENCE: 47
agggctcact gtgggtttt                                        19

<210> SEQ ID NO 48
<211> LENGTH: 20
<212> TYPE: DNA
<213> ORGANISM: Artificial Sequence
<220> FEATURE:
<223> OTHER INFORMATION: VH Primers

<400> SEQUENCE: 48
agagtcgagt caccatatcc                                       20

<210> SEQ ID NO 49
<211> LENGTH: 19
<212> TYPE: DNA
<213> ORGANISM: Artificial Sequence
<220> FEATURE:
<223> OTHER INFORMATION: VH Primers

<400> SEQUENCE: 49
cagctcccag atgtgagta                                        19

<210> SEQ ID NO 50
<211> LENGTH: 16
<212> TYPE: DNA
<213> ORGANISM: Artificial Sequence
<220> FEATURE:
<223> OTHER INFORMATION: VH Primers

<400> SEQUENCE: 50
gtctctggtg gctccg                                           16

<210> SEQ ID NO 51
<211> LENGTH: 20
<212> TYPE: DNA
<213> ORGANISM: Artificial Sequence
<220> FEATURE:
<223> OTHER INFORMATION: VH Primers

<400> SEQUENCE: 51
ctggtgactc tgataccaga                                       20

<210> SEQ ID NO 52
<211> LENGTH: 23
<212> TYPE: DNA
<213> ORGANISM: Artificial Sequence
<220> FEATURE:
<223> OTHER INFORMATION: VH Primers

<400> SEQUENCE: 52
atcctagtga ctcttatacc aac                                   23

<210> SEQ ID NO 53
<211> LENGTH: 20
<212> TYPE: DNA
<213> ORGANISM: Artificial Sequence
<220> FEATURE:
<223> OTHER INFORMATION: VH Primers

<400> SEQUENCE: 53
catactacag gtccaagtgg                                               20

<210> SEQ ID NO 54
<211> LENGTH: 19
<212> TYPE: DNA
<213> ORGANISM: Artificial Sequence
<220> FEATURE:
<223> OTHER INFORMATION: VH Primers

<400> SEQUENCE: 54
gatcaacacc aacactggg                                                19

<210> SEQ ID NO 55
<211> LENGTH: 18
<212> TYPE: DNA
<213> ORGANISM: Artificial Sequence
<220> FEATURE:
<223> OTHER INFORMATION: JH Primers

<400> SEQUENCE: 55
tccccaagtc tgaagcca                                                 18

<210> SEQ ID NO 56
<211> LENGTH: 15
<212> TYPE: DNA
<213> ORGANISM: Artificial Sequence
<220> FEATURE:
<223> OTHER INFORMATION: JH Primers

<400> SEQUENCE: 56
acatggctcc ccgct                                                    15

<210> SEQ ID NO 57
<211> LENGTH: 16
<212> TYPE: DNA
<213> ORGANISM: Artificial Sequence
<220> FEATURE:
<223> OTHER INFORMATION: JH Primers

<400> SEQUENCE: 57 ggaggggget gcagtg                                                   16

<210> SEQ ID NO 58
<211> LENGTH: 16
<212> TYPE: DNA
<213> ORGANISM: Artificial Sequence
<220> FEATURE:
<223> OTHER INFORMATION: JH Primers

<400> SEQUENCE: 58
ggctggtgct ggacag                                                   16

<210> SEQ ID NO 59
<211> LENGTH: 19
<212> TYPE: DNA
<213> ORGANISM: Artificial Sequence
<220> FEATURE:

<223> OTHER INFORMATION: JH Primers

<400> SEQUENCE: 59
agaaaggagg cagaaggaa                                                19

<210> SEQ ID NO 60
<211> LENGTH: 17
<212> TYPE: DNA
<213> ORGANISM: Artificial Sequence
<220> FEATURE:
<223> OTHER INFORMATION: JH Primers

<400> SEQUENCE: 60
cccagctcca ggacaga                                                  17

<210> SEQ ID NO 61
<211> LENGTH: 19
<212> TYPE: DNA
<213> ORGANISM: Artificial Sequence
<220> FEATURE:
<223> OTHER INFORMATION: JH Primers

<400> SEQUENCE: 61
gaaaggaggc agaaggaaa                                                19

<210> SEQ ID NO 62
<211> LENGTH: 18
<212> TYPE: DNA
<213> ORGANISM: Artificial Sequence
<220> FEATURE:
<223> OTHER INFORMATION: JH Primers

<400> SEQUENCE: 62
tcgagttaac ggaggaga                                                 18

<210> SEQ ID NO 63
<211> LENGTH: 19
<212> TYPE: DNA
<213> ORGANISM: Artificial Sequence
<220> FEATURE:
<223> OTHER INFORMATION: JH Primers

<400> SEQUENCE: 63
aaacctcgag ttaacggag                                                19

<210> SEQ ID NO 64
<211> LENGTH: 19
<212> TYPE: DNA
<213> ORGANISM: Artificial Sequence
<220> FEATURE:
<223> OTHER INFORMATION: JH Primers

<400> SEQUENCE: 64
aaatgcagca aaacccttc                                                19

<210> SEQ ID NO 65
<211> LENGTH: 17
<212> TYPE: DNA
<213> ORGANISM: Artificial Sequence
<220> FEATURE:
<223> OTHER INFORMATION: JH Primers

<400> SEQUENCE: 65
ggggctctct tggcagg                                                  17

<210> SEQ ID NO 66
<211> LENGTH: 16
<212> TYPE: DNA
<213> ORGANISM: Artificial Sequence
<220> FEATURE:
<223> OTHER INFORMATION: JH Primers

<400> SEQUENCE: 66
tccggggctc tcttgg                                               16

<210> SEQ ID NO 67
<211> LENGTH: 24
<212> TYPE: DNA
<213> ORGANISM: Artificial Sequence
<220> FEATURE:
<223> OTHER INFORMATION: JH Primers

<400> SEQUENCE: 67
tgctccgggg ctctcttggc agga                                      24

<210> SEQ ID NO 68
<211> LENGTH: 16
<212> TYPE: DNA
<213> ORGANISM: Artificial Sequence
<220> FEATURE:
<223> OTHER INFORMATION: JH Primers

<400> SEQUENCE: 68
gagttaaagg aggaga                                               16

<210> SEQ ID NO 69
<211> LENGTH: 17
<212> TYPE: DNA
<213> ORGANISM: Artificial Sequence
<220> FEATURE:
<223> OTHER INFORMATION: JH Primers

<400> SEQUENCE: 69
cccccagcac ccttatt                                              17

<210> SEQ ID NO 70
<211> LENGTH: 17
<212> TYPE: DNA
<213> ORGANISM: Artificial Sequence
<220> FEATURE:
<223> OTHER INFORMATION: JH Primers

<400> SEQUENCE: 70
gcaagctgag tctccct                                              17

<210> SEQ ID NO 71
<211> LENGTH: 19
<212> TYPE: DNA
<213> ORGANISM: Artificial Sequence
<220> FEATURE:
<223> OTHER INFORMATION: JH Primers

<400> SEQUENCE: 71
gtctccctaa gtggactca                                            19

<210> SEQ ID NO 72
<211> LENGTH: 18
<212> TYPE: DNA
<213> ORGANISM: Artificial Sequence
<220> FEATURE:
<223> OTHER INFORMATION: JH Primers

```
<400> SEQUENCE: 72
acaaaggccc tagagtgg                                                        18

<210> SEQ ID NO 73
<211> LENGTH: 18
<212> TYPE: DNA
<213> ORGANISM: Artificial Sequence
<220> FEATURE:
<223> OTHER INFORMATION: JH Primers

<400> SEQUENCE: 73 aaacccaca ggcagtag                                                         18

<210> SEQ ID NO 74
<211> LENGTH: 17
<212> TYPE: DNA
<213> ORGANISM: Artificial Sequence
<220> FEATURE:
<223> OTHER INFORMATION: JH Primers

<400> SEQUENCE: 74
cgacctcctt tgctgag                                                         17

<210> SEQ ID NO 75
<211> LENGTH: 16
<212> TYPE: DNA
<213> ORGANISM: Artificial Sequence
<220> FEATURE:
<223> OTHER INFORMATION: JH Primers

<400> SEQUENCE: 75
ggctgcagac cccaga                                                          16

<210> SEQ ID NO 76
<211> LENGTH: 16
<212> TYPE: DNA
<213> ORGANISM: Artificial Sequence
<220> FEATURE:
<223> OTHER INFORMATION: JH Primers

<400> SEQUENCE: 76
cagcgcagac caagga                                                          16

<210> SEQ ID NO 77
<211> LENGTH: 17
<212> TYPE: DNA
<213> ORGANISM: Artificial Sequence
<220> FEATURE:
<223> OTHER INFORMATION: JH Primers

<400> SEQUENCE: 77
ttgcccctcg tctgtgt                                                         17

<210> SEQ ID NO 78
<211> LENGTH: 20
<212> TYPE: DNA
<213> ORGANISM: Artificial Sequence
<220> FEATURE:
<223> OTHER INFORMATION: JH Primers

<400> SEQUENCE: 78
ctttctttcc tgacctccaa                                                      20

<210> SEQ ID NO 79
<211> LENGTH: 17
```

<212> TYPE: DNA
<213> ORGANISM: Artificial Sequence
<220> FEATURE:
<223> OTHER INFORMATION: JH Primers

<400> SEQUENCE: 79
cccacaggca gtagcag                                                  17

<210> SEQ ID NO 80
<211> LENGTH: 9
<212> TYPE: DNA
<213> ORGANISM: Artificial Sequence
<220> FEATURE:
<223> OTHER INFORMATION: DH primers for V-D-J rearrangements

<400> SEQUENCE: 80 ggtacaact                                                            9

<210> SEQ ID NO 81
<211> LENGTH: 12
<212> TYPE: DNA
<213> ORGANISM: Artificial Sequence
<220> FEATURE:
<223> OTHER INFORMATION: DH primers for V-D-J rearrangements

<400> SEQUENCE: 81
ggtacaactg ga                                                       12

<210> SEQ ID NO 82
<211> LENGTH: 15
<212> TYPE: DNA
<213> ORGANISM: Artificial Sequence
<220> FEATURE:
<223> OTHER INFORMATION: DH primers for V-D-J rearrangements

<400> SEQUENCE: 82
ggtataactg gaact                                                    15

<210> SEQ ID NO 83
<211> LENGTH: 12
<212> TYPE: DNA
<213> ORGANISM: Artificial Sequence
<220> FEATURE:
<223> OTHER INFORMATION: DH primers for V-D-J rearrangements

<400> SEQUENCE: 83
ggtataactg ga                                                       12

<210> SEQ ID NO 84
<211> LENGTH: 9
<212> TYPE: DNA
<213> ORGANISM: Artificial Sequence
<220> FEATURE:
<223> OTHER INFORMATION: DH primers for V-D-J rearrangements

<400> SEQUENCE: 84 ggtataacc                                                            9

<210> SEQ ID NO 85
<211> LENGTH: 12
<212> TYPE: DNA
<213> ORGANISM: Artificial Sequence
<220> FEATURE:
<223> OTHER INFORMATION: DH primers for V-D-J rearrangements

<400> SEQUENCE: 85
ggtataaccg ga                                                      12

<210> SEQ ID NO 86
<211> LENGTH: 15
<212> TYPE: DNA
<213> ORGANISM: Artificial Sequence
<220> FEATURE:
<223> OTHER INFORMATION: DH primers for V-D-J rearrangements

<400> SEQUENCE: 86
ggtataactg gaacg                                                   15

<210> SEQ ID NO 87
<211> LENGTH: 13
<212> TYPE: DNA
<213> ORGANISM: Artificial Sequence
<220> FEATURE:
<223> OTHER INFORMATION: DH primers for V-D-J rearrangements

<400> SEQUENCE: 87
ggtatagtgg gag                                                     13

<210> SEQ ID NO 88
<211> LENGTH: 17
<212> TYPE: DNA
<213> ORGANISM: Artificial Sequence
<220> FEATURE:
<223> OTHER INFORMATION: DH primers for V-D-J rearrangements

<400> SEQUENCE: 88
ggtatagtgg gagctac                                                 17

<210> SEQ ID NO 89
<211> LENGTH: 22
<212> TYPE: DNA
<213> ORGANISM: Artificial Sequence
<220> FEATURE:
<223> OTHER INFORMATION: DH primers for V-D-J rearrangements

<400> SEQUENCE: 89
aggatattgt agtagtacca gc                                           22

<210> SEQ ID NO 90
<211> LENGTH: 19
<212> TYPE: DNA
<213> ORGANISM: Artificial Sequence
<220> FEATURE:
<223> OTHER INFORMATION: DH primers for V-D-J rearrangements

<400> SEQUENCE: 90
aggatattgt agtagtacc                                               19

<210> SEQ ID NO 91
<211> LENGTH: 22
<212> TYPE: DNA
<213> ORGANISM: Artificial Sequence
<220> FEATURE:
<223> OTHER INFORMATION: DH primers for V-D-J rearrangements

<400> SEQUENCE: 91
aggatattgt actaatggtg ta                                           22

<210> SEQ ID NO 92
<211> LENGTH: 25
<212> TYPE: DNA
<213> ORGANISM: Artificial Sequence

```
<220> FEATURE:
<223> OTHER INFORMATION: DH primers for V-D-J rearrangements

<400> SEQUENCE: 92
aggatattgt actaatggtg tatgc                                 25

<210> SEQ ID NO 93
<211> LENGTH: 22
<212> TYPE: DNA
<213> ORGANISM: Artificial Sequence
<220> FEATURE:
<223> OTHER INFORMATION: DH primers for V-D-J rearrangements

<400> SEQUENCE: 93
aggatattgt agtggtggta gc                                    22

<210> SEQ ID NO 94
<211> LENGTH: 24
<212> TYPE: DNA
<213> ORGANISM: Artificial Sequence
<220> FEATURE:
<223> OTHER INFORMATION: DH primers for V-D-J rearrangements

<400> SEQUENCE: 94
aggatattgt agtggtggta gctg                                  24

<210> SEQ ID NO 95
<211> LENGTH: 14
<212> TYPE: DNA
<213> ORGANISM: Artificial Sequence
<220> FEATURE:
<223> OTHER INFORMATION: DH primers for V-D-J rearrangements

<400> SEQUENCE: 95
agcatattgt ggtg                                             14

<210> SEQ ID NO 96
<211> LENGTH: 18
<212> TYPE: DNA
<213> ORGANISM: Artificial Sequence
<220> FEATURE:
<223> OTHER INFORMATION: DH primers for V-D-J rearrangements

<400> SEQUENCE: 96
agcatattgt ggtggtga                                         18

<210> SEQ ID NO 97
<211> LENGTH: 17
<212> TYPE: DNA
<213> ORGANISM: Artificial Sequence
<220> FEATURE:
<223> OTHER INFORMATION: DH primers for V-D-J rearrangements

<400> SEQUENCE: 97
gtattactat ttttgga                                          17

<210> SEQ ID NO 98
<211> LENGTH: 20
<212> TYPE: DNA
<213> ORGANISM: Artificial Sequence
<220> FEATURE:
<223> OTHER INFORMATION: DH primers for V-D-J rearrangements

<400> SEQUENCE: 98
gtattacgat ttttggagtg                                       20
```

<210> SEQ ID NO 99
<211> LENGTH: 18
<212> TYPE: DNA
<213> ORGANISM: Artificial Sequence
<220> FEATURE:
<223> OTHER INFORMATION: DH primers for V-D-J rearrangements

<400> SEQUENCE: 99
gtattacgat attttgac                                               18

<210> SEQ ID NO 100
<211> LENGTH: 20
<212> TYPE: DNA
<213> ORGANISM: Artificial Sequence
<220> FEATURE:
<223> OTHER INFORMATION: DH primers for V-D-J rearrangements

<400> SEQUENCE: 100
gtattacgat attttgactg                                             20

<210> SEQ ID NO 101
<211> LENGTH: 20
<212> TYPE: DNA
<213> ORGANISM: Artificial Sequence
<220> FEATURE:
<223> OTHER INFORMATION: DH primers for V-D-J rearrangements

<400> SEQUENCE: 101
gtattacgat ggttcgggga                                             20

<210> SEQ ID NO 102
<211> LENGTH: 15
<212> TYPE: DNA
<213> ORGANISM: Artificial Sequence
<220> FEATURE:
<223> OTHER INFORMATION: DH primers for V-D-J rearrangements

<400> SEQUENCE: 102
gtattactat ggttc                                                  15

<210> SEQ ID NO 103
<211> LENGTH: 18
<212> TYPE: DNA
<213> ORGANISM: Artificial Sequence
<220> FEATURE:
<223> OTHER INFORMATION: DH primers for V-D-J rearrangements

<400> SEQUENCE: 103
gttatgatta cgtttggg                                               18

<210> SEQ ID NO 104
<211> LENGTH: 21
<212> TYPE: DNA
<213> ORGANISM: Artificial Sequence
<220> FEATURE:
<223> OTHER INFORMATION: DH primers for V-D-J rearrangements

<400> SEQUENCE: 104
gttatgatta cgtttggggg a                                           21

<210> SEQ ID NO 105
<211> LENGTH: 15
<212> TYPE: DNA
<213> ORGANISM: Artificial Sequence
<220> FEATURE:
<223> OTHER INFORMATION: DH primers for V-D-J rearrangements

```
<400> SEQUENCE: 105
gtattactat gatag                                               15

<210> SEQ ID NO 106
<211> LENGTH: 20
<212> TYPE: DNA
<213> ORGANISM: Artificial Sequence
<220> FEATURE:
<223> OTHER INFORMATION: DH primers for V-D-J rearrangements

<400> SEQUENCE: 106
gtattactat gatagtagtg                                          20

<210> SEQ ID NO 107
<211> LENGTH: 11
<212> TYPE: DNA
<213> ORGANISM: Artificial Sequence
<220> FEATURE:
<223> OTHER INFORMATION: DH primers for V-D-J rearrangements

<400> SEQUENCE: 107
tgactacagt a                                                   11

<210> SEQ ID NO 108
<211> LENGTH: 13
<212> TYPE: DNA
<213> ORGANISM: Artificial Sequence
<220> FEATURE:
<223> OTHER INFORMATION: DH primers for V-D-J rearrangements

<400> SEQUENCE: 108
tgactacagt aac                                                 13

<210> SEQ ID NO 109
<211> LENGTH: 11
<212> TYPE: DNA
<213> ORGANISM: Artificial Sequence
<220> FEATURE:
<223> OTHER INFORMATION: DH primers for V-D-J rearrangements

<400> SEQUENCE: 109
tgactacggt g                                                   11

<210> SEQ ID NO 110
<211> LENGTH: 14
<212> TYPE: DNA
<213> ORGANISM: Artificial Sequence
<220> FEATURE:
<223> OTHER INFORMATION: DH primers for V-D-J rearrangements

<400> SEQUENCE: 110
tgactacggt gact                                                14

<210> SEQ ID NO 111
<211> LENGTH: 13
<212> TYPE: DNA
<213> ORGANISM: Artificial Sequence
<220> FEATURE:
<223> OTHER INFORMATION: DH primers for V-D-J rearrangements

<400> SEQUENCE: 111
tgactacggt ggt                                                 13

<210> SEQ ID NO 112
```

```
<211> LENGTH: 15
<212> TYPE: DNA
<213> ORGANISM: Artificial Sequence
<220> FEATURE:
<223> OTHER INFORMATION: DH primers for V-D-J rearrangements

<400> SEQUENCE: 112
tgactacggt ggtta                                                         15

<210> SEQ ID NO 113
<211> LENGTH: 9
<212> TYPE: DNA
<213> ORGANISM: Artificial Sequence
<220> FEATURE:
<223> OTHER INFORMATION: DH primers for V-D-J rearrangements

<400> SEQUENCE: 113 gtggataca                                                                 9

<210> SEQ ID NO 114
<211> LENGTH: 12
<212> TYPE: DNA
<213> ORGANISM: Artificial Sequence
<220> FEATURE:
<223> OTHER INFORMATION: DH primers for V-D-J rearrangements

<400> SEQUENCE: 114
gtggatatag ct                                                            12

<210> SEQ ID NO 115
<211> LENGTH: 17
<212> TYPE: DNA
<213> ORGANISM: Artificial Sequence
<220> FEATURE:
<223> OTHER INFORMATION: DH primers for V-D-J rearrangements

<400> SEQUENCE: 115
gtggatatag tggctac                                                       17

<210> SEQ ID NO 116
<211> LENGTH: 20
<212> TYPE: DNA
<213> ORGANISM: Artificial Sequence
<220> FEATURE:
<223> OTHER INFORMATION: DH primers for V-D-J rearrangements

<400> SEQUENCE: 116
gtggatatag tggctacgat                                                    20

<210> SEQ ID NO 117
<211> LENGTH: 9
<212> TYPE: DNA
<213> ORGANISM: Artificial Sequence
<220> FEATURE:
<223> OTHER INFORMATION: DH primers for V-D-J rearrangements

<400> SEQUENCE: 117 gtagagatg                                                                 9

<210> SEQ ID NO 118
<211> LENGTH: 15
<212> TYPE: DNA
<213> ORGANISM: Artificial Sequence
<220> FEATURE:
<223> OTHER INFORMATION: DH primers for V-D-J rearrangements

<400> SEQUENCE: 118
```
gtagagatgg ctaca                                              15

<210> SEQ ID NO 119
<211> LENGTH: 13
<212> TYPE: DNA
<213> ORGANISM: Artificial Sequence
<220> FEATURE:
<223> OTHER INFORMATION: DH primers for V-D-J rearrangements

<400> SEQUENCE: 119
gagtatagca gct                                                13

<210> SEQ ID NO 120
<211> LENGTH: 16
<212> TYPE: DNA
<213> ORGANISM: Artificial Sequence
<220> FEATURE:
<223> OTHER INFORMATION: DH primers for V-D-J rearrangements

<400> SEQUENCE: 120
gagtatagca gctgct                                             16

<210> SEQ ID NO 121
<211> LENGTH: 13
<212> TYPE: DNA
<213> ORGANISM: Artificial Sequence
<220> FEATURE:
<223> OTHER INFORMATION: DH primers for V-D-J rearrangements

<400> SEQUENCE: 121
gggtatagca gca                                                13

<210> SEQ ID NO 122
<211> LENGTH: 17
<212> TYPE: DNA
<213> ORGANISM: Artificial Sequence
<220> FEATURE:
<223> OTHER INFORMATION: DH primers for V-D-J rearrangements

<400> SEQUENCE: 122
gggtatagca gcagctg                                            17

<210> SEQ ID NO 123
<211> LENGTH: 14
<212> TYPE: DNA
<213> ORGANISM: Artificial Sequence
<220> FEATURE:
<223> OTHER INFORMATION: DH primers for V-D-J rearrangements

<400> SEQUENCE: 123
gggtatagca gtgg                                               14

<210> SEQ ID NO 124
<211> LENGTH: 18
<212> TYPE: DNA
<213> ORGANISM: Artificial Sequence
<220> FEATURE:
<223> OTHER INFORMATION: DH primers for V-D-J rearrangements

<400> SEQUENCE: 124
gggtatagca gtggctgg                                           18

<210> SEQ ID NO 125
<211> LENGTH: 14
<212> TYPE: DNA

<213> ORGANISM: Artificial Sequence
<220> FEATURE:
<223> OTHER INFORMATION: DH primers for V-D-J rearrangements

<400> SEQUENCE: 125
gggtatagca gcgg                                                          14

<210> SEQ ID NO 126
<211> LENGTH: 8
<212> TYPE: DNA
<213> ORGANISM: Artificial Sequence
<220> FEATURE:
<223> OTHER INFORMATION: DH primers for V-D-J rearrangements

<400> SEQUENCE: 126 ctaactgg                                                                 8

<210> SEQ ID NO 127
<211> LENGTH: 10
<212> TYPE: DNA
<213> ORGANISM: Artificial Sequence
<220> FEATURE:
<223> OTHER INFORMATION: DH primers for V-D-J rearrangements

<400> SEQUENCE: 127
ctaactgggg                                                               10

<210> SEQ ID NO 128
<211> LENGTH: 13
<212> TYPE: DNA
<213> ORGANISM: Artificial Sequence
<220> FEATURE:
<223> OTHER INFORMATION: DH primers for V-D-J rearrangements

<400> SEQUENCE: 128
aacgacggcc agt                                                           13

<210> SEQ ID NO 129
<211> LENGTH: 22
<212> TYPE: DNA
<213> ORGANISM: Artificial Sequence
<220> FEATURE:
<223> OTHER INFORMATION: DH primers for V-D-J rearrangements

<400> SEQUENCE: 129
aacgacggcc agtggtacaa ct                                                 22

<210> SEQ ID NO 130
<211> LENGTH: 25
<212> TYPE: DNA
<213> ORGANISM: Artificial Sequence
<220> FEATURE:
<223> OTHER INFORMATION: DH primers for V-D-J rearrangements

<400> SEQUENCE: 130
aacgacggcc agtggtacaa ctgga                                              25

<210> SEQ ID NO 131
<211> LENGTH: 28
<212> TYPE: DNA
<213> ORGANISM: Artificial Sequence
<220> FEATURE:
<223> OTHER INFORMATION: DH primers for V-D-J rearrangements

<400> SEQUENCE: 131
aacgacggcc agtggtataa ctggaact                                           28

<210> SEQ ID NO 132
<211> LENGTH: 25
<212> TYPE: DNA
<213> ORGANISM: Artificial Sequence
<220> FEATURE:
<223> OTHER INFORMATION: DH primers for V-D-J rearrangements

<400> SEQUENCE: 132
aacgacggcc agtggtataa ctgga                                    25

<210> SEQ ID NO 133
<211> LENGTH: 22
<212> TYPE: DNA
<213> ORGANISM: Artificial Sequence
<220> FEATURE:
<223> OTHER INFORMATION: DH primers for V-D-J rearrangements

<400> SEQUENCE: 133
aacgacggcc agtggtataa cc                                       22

<210> SEQ ID NO 134
<211> LENGTH: 25
<212> TYPE: DNA
<213> ORGANISM: Artificial Sequence
<220> FEATURE:
<223> OTHER INFORMATION: DH primers for V-D-J rearrangements

<400> SEQUENCE: 134
aacgacggcc agtggtataa ccgga                                    25

<210> SEQ ID NO 135
<211> LENGTH: 28
<212> TYPE: DNA
<213> ORGANISM: Artificial Sequence
<220> FEATURE:
<223> OTHER INFORMATION: DH primers for V-D-J rearrangements

<400> SEQUENCE: 135
aacgacggcc agtggtataa ctggaacg                                 28

<210> SEQ ID NO 136
<211> LENGTH: 26
<212> TYPE: DNA
<213> ORGANISM: Artificial Sequence
<220> FEATURE:
<223> OTHER INFORMATION: DH primers for V-D-J rearrangements

<400> SEQUENCE: 136
aacgacggcc agtggtatag tgggag                                   26

<210> SEQ ID NO 137
<211> LENGTH: 30
<212> TYPE: DNA
<213> ORGANISM: Artificial Sequence
<220> FEATURE:
<223> OTHER INFORMATION: DH primers for V-D-J rearrangements

<400> SEQUENCE: 137
aacgacggcc agtggtatag tgggagctac                               30

<210> SEQ ID NO 138
<211> LENGTH: 34
<212> TYPE: DNA
<213> ORGANISM: Artificial Sequence
<220> FEATURE:

```
<223> OTHER INFORMATION: DH primers for V-D-J rearrangements

<400> SEQUENCE: 138
aacgacggcc agtggatatt gtagtagtac cagc                              34

<210> SEQ ID NO 139
<211> LENGTH: 32
<212> TYPE: DNA
<213> ORGANISM: Artificial Sequence
<220> FEATURE:
<223> OTHER INFORMATION: DH primers for V-D-J rearrangements

<400> SEQUENCE: 139
aacgacggcc agtaggatat tgtagtagta cc                                32

<210> SEQ ID NO 140
<211> LENGTH: 35
<212> TYPE: DNA
<213> ORGANISM: Artificial Sequence
<220> FEATURE:
<223> OTHER INFORMATION: DH primers for V-D-J rearrangements

<400> SEQUENCE: 140
aacgacggcc agtaggatat tgtactaatg gtgta                             35

<210> SEQ ID NO 141
<211> LENGTH: 36
<212> TYPE: DNA
<213> ORGANISM: Artificial Sequence
<220> FEATURE:
<223> OTHER INFORMATION: DH primers for V-D-J rearrangements

<400> SEQUENCE: 141
aacgacggcc agtgatattg tactaatggt gtatgc                            36

<210> SEQ ID NO 142
<211> LENGTH: 33
<212> TYPE: DNA
<213> ORGANISM: Artificial Sequence
<220> FEATURE:
<223> OTHER INFORMATION: DH primers for V-D-J rearrangements

<400> SEQUENCE: 142
aacgacggcc agtgatattg tagtggtggt agc                               33

<210> SEQ ID NO 143
<211> LENGTH: 34
<212> TYPE: DNA
<213> ORGANISM: Artificial Sequence
<220> FEATURE:
<223> OTHER INFORMATION: DH primers for V-D-J rearrangements

<400> SEQUENCE: 143
aacgacggcc agtatattgt agtggtggta gctg                              34

<210> SEQ ID NO 144
<211> LENGTH: 27
<212> TYPE: DNA
<213> ORGANISM: Artificial Sequence
<220> FEATURE:
<223> OTHER INFORMATION: DH primers for V-D-J rearrangements

<400> SEQUENCE: 144
aacgacggcc agtagcatat tgtggtg                                      27
```

```
<210> SEQ ID NO 145
<211> LENGTH: 31
<212> TYPE: DNA
<213> ORGANISM: Artificial Sequence
<220> FEATURE:
<223> OTHER INFORMATION: DH primers for V-D-J rearrangements

<400> SEQUENCE: 145
aacgacggcc agtagcatat tgtggtggtg a                                31

<210> SEQ ID NO 146
<211> LENGTH: 30
<212> TYPE: DNA
<213> ORGANISM: Artificial Sequence
<220> FEATURE:
<223> OTHER INFORMATION: DH primers for V-D-J rearrangements

<400> SEQUENCE: 146
aacgacggcc agtgtattac gattttgga                                   30

<210> SEQ ID NO 147
<211> LENGTH: 33
<212> TYPE: DNA
<213> ORGANISM: Artificial Sequence
<220> FEATURE:
<223> OTHER INFORMATION: DH primers for V-D-J rearrangements

<400> SEQUENCE: 147
aacgacggcc agtgtattac gattttgga gtg                               33

<210> SEQ ID NO 148
<211> LENGTH: 31
<212> TYPE: DNA
<213> ORGANISM: Artificial Sequence
<220> FEATURE:
<223> OTHER INFORMATION: DH primers for V-D-J rearrangements

<400> SEQUENCE: 148
aacgacggcc agtgtattac gatattttga c                                31

<210> SEQ ID NO 149
<211> LENGTH: 33
<212> TYPE: DNA
<213> ORGANISM: Artificial Sequence
<220> FEATURE:
<223> OTHER INFORMATION: DH primers for V-D-J rearrangements

<400> SEQUENCE: 149
aacgacggcc agtgtattac gatattttga ctg                              33

<210> SEQ ID NO 150
<211> LENGTH: 33
<212> TYPE: DNA
<213> ORGANISM: Artificial Sequence
<220> FEATURE:
<223> OTHER INFORMATION: DH primers for V-D-J rearrangements

<400> SEQUENCE: 150
aacgacggcc agtgtattac tatggttcgg gga                              33

<210> SEQ ID NO 151
<211> LENGTH: 28
<212> TYPE: DNA
<213> ORGANISM: Artificial Sequence
<220> FEATURE:
<223> OTHER INFORMATION: DH primers for V-D-J rearrangements
```

<400> SEQUENCE: 151
aacgacggcc agtgtattac tatggttc                                28

<210> SEQ ID NO 152
<211> LENGTH: 31
<212> TYPE: DNA
<213> ORGANISM: Artificial Sequence
<220> FEATURE:
<223> OTHER INFORMATION: DH primers for V-D-J rearrangements

<400> SEQUENCE: 152
aacgacggcc agtgttatga ttacgtttgg g                            31

<210> SEQ ID NO 153
<211> LENGTH: 34
<212> TYPE: DNA
<213> ORGANISM: Artificial Sequence
<220> FEATURE:
<223> OTHER INFORMATION: DH primers for V-D-J rearrangements

<400> SEQUENCE: 153
aacgacggcc agtgttatga ttacgtttgg ggga                         34

<210> SEQ ID NO 154
<211> LENGTH: 28
<212> TYPE: DNA
<213> ORGANISM: Artificial Sequence
<220> FEATURE:
<223> OTHER INFORMATION: DH primers for V-D-J rearrangements

<400> SEQUENCE: 154
aacgacggcc agtgtattac tatgatag                                28

<210> SEQ ID NO 155
<211> LENGTH: 33
<212> TYPE: DNA
<213> ORGANISM: Artificial Sequence
<220> FEATURE:
<223> OTHER INFORMATION: DH primers for V-D-J rearrangements

<400> SEQUENCE: 155
aacgacggcc agtgtattac tatgatagta gtg                          33

<210> SEQ ID NO 156
<211> LENGTH: 24
<212> TYPE: DNA
<213> ORGANISM: Artificial Sequence
<220> FEATURE:
<223> OTHER INFORMATION: DH primers for V-D-J rearrangements

<400> SEQUENCE: 156
aacgacggcc agttgactac agta                                    24

<210> SEQ ID NO 157
<211> LENGTH: 26
<212> TYPE: DNA
<213> ORGANISM: Artificial Sequence
<220> FEATURE:
<223> OTHER INFORMATION: DH primers for V-D-J rearrangements

<400> SEQUENCE: 157
aacgacggcc agttgactac agtaac                                  26

<210> SEQ ID NO 158
<211> LENGTH: 24

```
<212> TYPE: DNA
<213> ORGANISM: Artificial Sequence
<220> FEATURE:
<223> OTHER INFORMATION: DH primers for V-D-J rearrangements

<400> SEQUENCE: 158
aacgacggcc agttgactac ggtg                                    24

<210> SEQ ID NO 159
<211> LENGTH: 27
<212> TYPE: DNA
<213> ORGANISM: Artificial Sequence
<220> FEATURE:
<223> OTHER INFORMATION: DH primers for V-D-J rearrangements

<400> SEQUENCE: 159
aacgacggcc agttgactac ggtgact                                 27

<210> SEQ ID NO 160
<211> LENGTH: 26
<212> TYPE: DNA
<213> ORGANISM: Artificial Sequence
<220> FEATURE:
<223> OTHER INFORMATION: DH primers for V-D-J rearrangements

<400> SEQUENCE: 160
aacgacggcc agttgactac ggtggt                                  26

<210> SEQ ID NO 161
<211> LENGTH: 28
<212> TYPE: DNA
<213> ORGANISM: Artificial Sequence
<220> FEATURE:
<223> OTHER INFORMATION: DH primers for V-D-J rearrangements

<400> SEQUENCE: 161
aacgacggcc agttgactac ggtggtta                                28

<210> SEQ ID NO 162
<211> LENGTH: 22
<212> TYPE: DNA
<213> ORGANISM: Artificial Sequence
<220> FEATURE:
<223> OTHER INFORMATION: DH primers for V-D-J rearrangements

<400> SEQUENCE: 162
aacgacggcc agtgtggata ca                                      22

<210> SEQ ID NO 163
<211> LENGTH: 25
<212> TYPE: DNA
<213> ORGANISM: Artificial Sequence
<220> FEATURE:
<223> OTHER INFORMATION: DH primers for V-D-J rearrangements

<400> SEQUENCE: 163
aacgacggcc agtgtggata cagct                                   25

<210> SEQ ID NO 164
<211> LENGTH: 30
<212> TYPE: DNA
<213> ORGANISM: Artificial Sequence
<220> FEATURE:
<223> OTHER INFORMATION: DH primers for V-D-J rearrangements

<400> SEQUENCE: 164
```

```
aacgacggcc agtgtggata tagtggctac                                    30
```

<210> SEQ ID NO 165
<211> LENGTH: 33
<212> TYPE: DNA
<213> ORGANISM: Artificial Sequence
<220> FEATURE:
<223> OTHER INFORMATION: DH primers for V-D-J rearrangements

<400> SEQUENCE: 165

```
aacgacggcc agtgtggata tagtggctac gat                                33
```

<210> SEQ ID NO 166
<211> LENGTH: 22
<212> TYPE: DNA
<213> ORGANISM: Artificial Sequence
<220> FEATURE:
<223> OTHER INFORMATION: DH primers for V-D-J rearrangements

<400> SEQUENCE: 166

```
aacgacggcc agtgtagaga tg                                            22
```

<210> SEQ ID NO 167
<211> LENGTH: 28
<212> TYPE: DNA
<213> ORGANISM: Artificial Sequence
<220> FEATURE:
<223> OTHER INFORMATION: DH primers for V-D-J rearrangements

<400> SEQUENCE: 167

```
aacgacggcc agtgtagaga tggctaca                                      28
```

<210> SEQ ID NO 168
<211> LENGTH: 26
<212> TYPE: DNA
<213> ORGANISM: Artificial Sequence
<220> FEATURE:
<223> OTHER INFORMATION: DH primers for V-D-J rearrangements

<400> SEQUENCE: 168

```
aacgacggcc agtgagtata gcagct                                        26
```

<210> SEQ ID NO 169
<211> LENGTH: 29
<212> TYPE: DNA
<213> ORGANISM: Artificial Sequence
<220> FEATURE:
<223> OTHER INFORMATION: DH primers for V-D-J rearrangements

<400> SEQUENCE: 169

```
aacgacggcc agtgagtata gcagctgct                                     29
```

<210> SEQ ID NO 170
<211> LENGTH: 26
<212> TYPE: DNA
<213> ORGANISM: Artificial Sequence
<220> FEATURE:
<223> OTHER INFORMATION: DH primers for V-D-J rearrangements

<400> SEQUENCE: 170

```
aacgacggcc agtgggtata gcagca                                        26
```

<210> SEQ ID NO 171
<211> LENGTH: 30
<212> TYPE: DNA
<213> ORGANISM: Artificial Sequence

```
<220> FEATURE:
<223> OTHER INFORMATION: DH primers for V-D-J rearrangements

<400> SEQUENCE: 171
aacgacggcc agtgggtata gcagcagctg                                30

<210> SEQ ID NO 172
<211> LENGTH: 27
<212> TYPE: DNA
<213> ORGANISM: Artificial Sequence
<220> FEATURE:
<223> OTHER INFORMATION: DH primers for V-D-J rearrangements

<400> SEQUENCE: 172
aacgacggcc agtgggtata gcagtgg                                   27

<210> SEQ ID NO 173
<211> LENGTH: 30
<212> TYPE: DNA
<213> ORGANISM: Artificial Sequence
<220> FEATURE:
<223> OTHER INFORMATION: DH primers for V-D-J rearrangements

<400> SEQUENCE: 173
aacgacggcc agtggtatag cagtggctgg                                30

<210> SEQ ID NO 174
<211> LENGTH: 27
<212> TYPE: DNA
<213> ORGANISM: Artificial Sequence
<220> FEATURE:
<223> OTHER INFORMATION: DH primers for V-D-J rearrangements

<400> SEQUENCE: 174
aacgacggcc agtgggtata gcagcgg                                   27

<210> SEQ ID NO 175
<211> LENGTH: 21
<212> TYPE: DNA
<213> ORGANISM: Artificial Sequence
<220> FEATURE:
<223> OTHER INFORMATION: DH primers for V-D-J rearrangements

<400> SEQUENCE: 175
aacgacggcc agtctaactg g                                         21

<210> SEQ ID NO 176
<211> LENGTH: 23
<212> TYPE: DNA
<213> ORGANISM: Artificial Sequence
<220> FEATURE:
<223> OTHER INFORMATION: DH primers for V-D-J rearrangements

<400> SEQUENCE: 176
aacgacggcc agtctaactg ggg                                       23

<210> SEQ ID NO 177
<211> LENGTH: 21
<212> TYPE: DNA
<213> ORGANISM: Artificial Sequence
<220> FEATURE:
<223> OTHER INFORMATION: TCR beta primers for individual V segments

<400> SEQUENCE: 177
agacagaaag ctaagaaatc c                                         21
```

<210> SEQ ID NO 178
<211> LENGTH: 19
<212> TYPE: DNA
<213> ORGANISM: Artificial Sequence
<220> FEATURE:
<223> OTHER INFORMATION: TCR beta primers for individual V segments

<400> SEQUENCE: 178
caaatcttgg ggcagaaag                                          19

<210> SEQ ID NO 179
<211> LENGTH: 27
<212> TYPE: DNA
<213> ORGANISM: Artificial Sequence
<220> FEATURE:
<223> OTHER INFORMATION: TCR beta primers for individual V segments

<400> SEQUENCE: 179
taagaaattt ctgaagataa tgtttag                                 27

<210> SEQ ID NO 180
<211> LENGTH: 20
<212> TYPE: DNA
<213> ORGANISM: Artificial Sequence
<220> FEATURE:
<223> OTHER INFORMATION: TCR beta primers for individual V segments

<400> SEQUENCE: 180
tctacagtaa caaggagcca                                         20

<210> SEQ ID NO 181
<211> LENGTH: 25
<212> TYPE: DNA
<213> ORGANISM: Artificial Sequence
<220> FEATURE:
<223> OTHER INFORMATION: TCR beta primers for individual V segments

<400> SEQUENCE: 181
ctatgagaaa ctctctataa atgaa                                   25

<210> SEQ ID NO 182
<211> LENGTH: 24
<212> TYPE: DNA
<213> ORGANISM: Artificial Sequence
<220> FEATURE:
<223> OTHER INFORMATION: TCR beta primers for individual V segments

<400> SEQUENCE: 182
tgtctacaac tttaaagaac agac                                    24

<210> SEQ ID NO 183
<211> LENGTH: 20
<212> TYPE: DNA
<213> ORGANISM: Artificial Sequence
<220> FEATURE:
<223> OTHER INFORMATION: TCR beta primers for individual V segments

<400> SEQUENCE: 183
tacagtcttg aagaacgggt                                         20

<210> SEQ ID NO 184
<211> LENGTH: 22
<212> TYPE: DNA
<213> ORGANISM: Artificial Sequence
<220> FEATURE:
<223> OTHER INFORMATION: TCR beta primers for individual V segments

```
<400> SEQUENCE: 184
tttgaatact tcagtgagac ac                                                22

<210> SEQ ID NO 185
<211> LENGTH: 22
<212> TYPE: DNA
<213> ORGANISM: Artificial Sequence
<220> FEATURE:
<223> OTHER INFORMATION: TCR beta primers for individual V segments

<400> SEQUENCE: 185
gctaatgagt taaggagatc ag                                                22

<210> SEQ ID NO 186
<211> LENGTH: 23
<212> TYPE: DNA
<213> ORGANISM: Artificial Sequence
<220> FEATURE:
<223> OTHER INFORMATION: TCR beta primers for individual V segments

<400> SEQUENCE: 186
agtattatag ggaggaagag aat                                               23

<210> SEQ ID NO 187
<211> LENGTH: 21
<212> TYPE: DNA
<213> ORGANISM: Artificial Sequence
<220> FEATURE:
<223> OTHER INFORMATION: TCR beta primers for individual V segments

<400> SEQUENCE: 187
tatgagaaag aagagagagg a                                                 21

<210> SEQ ID NO 188
<211> LENGTH: 19
<212> TYPE: DNA
<213> ORGANISM: Artificial Sequence
<220> FEATURE:
<223> OTHER INFORMATION: TCR beta primers for individual V segments

<400> SEQUENCE: 188
tgaggaggaa gagagacag                                                    19

<210> SEQ ID NO 189
<211> LENGTH: 19
<212> TYPE: DNA
<213> ORGANISM: Artificial Sequence
<220> FEATURE:
<223> OTHER INFORMATION: TCR beta primers for individual V segments

<400> SEQUENCE: 189
cctttggtat gacgagggt                                                    19

<210> SEQ ID NO 190
<211> LENGTH: 21
<212> TYPE: DNA
<213> ORGANISM: Artificial Sequence
<220> FEATURE:
<223> OTHER INFORMATION: TCR beta primers for individual V segments

<400> SEQUENCE: 190
gctgatttat tactcagctt c                                                 21

<210> SEQ ID NO 191
```

-continued

```
<211> LENGTH: 20
<212> TYPE: DNA
<213> ORGANISM: Artificial Sequence
<220> FEATURE:
<223> OTHER INFORMATION: TCR beta primers for individual V segments

<400> SEQUENCE: 191
actcagttgg tgagggtaca                                                20

<210> SEQ ID NO 192
<211> LENGTH: 21
<212> TYPE: DNA
<213> ORGANISM: Artificial Sequence
<220> FEATURE:
<223> OTHER INFORMATION: TCR beta primers for individual V segments

<400> SEQUENCE: 192
agatgtaccc aggatatgag a                                              21

<210> SEQ ID NO 193
<211> LENGTH: 19
<212> TYPE: DNA
<213> ORGANISM: Artificial Sequence
<220> FEATURE:
<223> OTHER INFORMATION: TCR beta primers for individual V segments

<400> SEQUENCE: 193
ggtgctggta tcactgacc                                                 19

<210> SEQ ID NO 194
<211> LENGTH: 16
<212> TYPE: DNA
<213> ORGANISM: Artificial Sequence
<220> FEATURE:
<223> OTHER INFORMATION: TCR beta primers for individual V segments

<400> SEQUENCE: 194
caggcatggg gctgaa                                                    16

<210> SEQ ID NO 195
<211> LENGTH: 16
<212> TYPE: DNA
<213> ORGANISM: Artificial Sequence
<220> FEATURE:
<223> OTHER INFORMATION: TCR beta primers for individual V segments

<400> SEQUENCE: 195
cagttgctgc tgctct                                                    16

<210> SEQ ID NO 196
<211> LENGTH: 20
<212> TYPE: DNA
<213> ORGANISM: Artificial Sequence
<220> FEATURE:
<223> OTHER INFORMATION: TCR beta primers for individual V segments

<400> SEQUENCE: 196
gctggtacta ctgacaaaga                                                20

<210> SEQ ID NO 197
<211> LENGTH: 15
<212> TYPE: DNA
<213> ORGANISM: Artificial Sequence
<220> FEATURE:
<223> OTHER INFORMATION: TCR beta primers for individual V segments

<400> SEQUENCE: 197
```

```
atggggctga ggcgc                                                    15

<210> SEQ ID NO 198
<211> LENGTH: 21
<212> TYPE: DNA
<213> ORGANISM: Artificial Sequence
<220> FEATURE:
<223> OTHER INFORMATION: TCR beta primers for individual V segments

<400> SEQUENCE: 198
aatttacttc caaggcaagg a                                             21

<210> SEQ ID NO 199
<211> LENGTH: 22
<212> TYPE: DNA
<213> ORGANISM: Artificial Sequence
<220> FEATURE:
<223> OTHER INFORMATION: TCR beta primers for individual V segments

<400> SEQUENCE: 199
taatttactt ccaaggcaac ag                                            22

<210> SEQ ID NO 200
<211> LENGTH: 16
<212> TYPE: DNA
<213> ORGANISM: Artificial Sequence
<220> FEATURE:
<223> OTHER INFORMATION: TCR beta primers for individual V segments

<400> SEQUENCE: 200
gggtgcggca gatgac                                                   16

<210> SEQ ID NO 201
<211> LENGTH: 20
<212> TYPE: DNA
<213> ORGANISM: Artificial Sequence
<220> FEATURE:
<223> OTHER INFORMATION: TCR beta primers for individual V segments

<400> SEQUENCE: 201
tgacttactc ccagagtgat                                               20

<210> SEQ ID NO 202
<211> LENGTH: 20
<212> TYPE: DNA
<213> ORGANISM: Artificial Sequence
<220> FEATURE:
<223> OTHER INFORMATION: TCR beta primers for individual V segments

<400> SEQUENCE: 202
gctcagtgat caattctcca                                               20

<210> SEQ ID NO 203
<211> LENGTH: 21
<212> TYPE: DNA
<213> ORGANISM: Artificial Sequence
<220> FEATURE:
<223> OTHER INFORMATION: TCR beta primers for individual V segments

<400> SEQUENCE: 203
cttcaattat gaagcccaac a                                             21

<210> SEQ ID NO 204
<211> LENGTH: 18
<212> TYPE: DNA
```

```
<213> ORGANISM: Artificial Sequence
<220> FEATURE:
<223> OTHER INFORMATION: TCR beta primers for individual V segments

<400> SEQUENCE: 204
gatcgcttct ttgcagaa                                                         18

<210> SEQ ID NO 205
<211> LENGTH: 22
<212> TYPE: DNA
<213> ORGANISM: Artificial Sequence
<220> FEATURE:
<223> OTHER INFORMATION: TCR beta primers for individual V segments

<400> SEQUENCE: 205
gaagctcaac tagaaaaatc aa                                                    22

<210> SEQ ID NO 206
<211> LENGTH: 17
<212> TYPE: DNA
<213> ORGANISM: Artificial Sequence
<220> FEATURE:
<223> OTHER INFORMATION: TCR beta primers for individual V segments

<400> SEQUENCE: 206
cgattctccg cacaaca                                                          17

<210> SEQ ID NO 207
<211> LENGTH: 23
<212> TYPE: DNA
<213> ORGANISM: Artificial Sequence
<220> FEATURE:
<223> OTHER INFORMATION: TCR beta primers for individual V segments

<400> SEQUENCE: 207
attactcata tggtgttcac gac                                                   23

<210> SEQ ID NO 208
<211> LENGTH: 18
<212> TYPE: DNA
<213> ORGANISM: Artificial Sequence
<220> FEATURE:
<223> OTHER INFORMATION: TCR beta primers for individual V segments

<400> SEQUENCE: 208
tcagcagctg ctgatatt                                                         18

<210> SEQ ID NO 209
<211> LENGTH: 19
<212> TYPE: DNA
<213> ORGANISM: Artificial Sequence
<220> FEATURE:
<223> OTHER INFORMATION: TCR beta primers for individual V segments

<400> SEQUENCE: 209
cacagagaca ggaacacca                                                        19

<210> SEQ ID NO 210
<211> LENGTH: 21
<212> TYPE: DNA
<213> ORGANISM: Artificial Sequence
<220> FEATURE:
<223> OTHER INFORMATION: TCR beta primers for individual V segments

<400> SEQUENCE: 210
gttcaatttc aggatgagag t                                                     21
```

<210> SEQ ID NO 211
<211> LENGTH: 22
<212> TYPE: DNA
<213> ORGANISM: Artificial Sequence
<220> FEATURE:
<223> OTHER INFORMATION: TCR beta primers for individual V segments

<400> SEQUENCE: 211
gattcagttt cagaataacg gt                                              22

<210> SEQ ID NO 212
<211> LENGTH: 22
<212> TYPE: DNA
<213> ORGANISM: Artificial Sequence
<220> FEATURE:
<223> OTHER INFORMATION: TCR beta primers for individual V segments

<400> SEQUENCE: 212
gattcgatat gagaatgagg aa                                              22

<210> SEQ ID NO 213
<211> LENGTH: 16
<212> TYPE: DNA
<213> ORGANISM: Artificial Sequence
<220> FEATURE:
<223> OTHER INFORMATION: TCR beta primers for individual V segments

<400> SEQUENCE: 213
ctgcagctgg accctc                                                     16

<210> SEQ ID NO 214
<211> LENGTH: 18
<212> TYPE: DNA
<213> ORGANISM: Artificial Sequence
<220> FEATURE:
<223> OTHER INFORMATION: TCR beta primers for individual V segments

<400> SEQUENCE: 214
gcaggtatgc ccacagag                                                   18

<210> SEQ ID NO 215
<211> LENGTH: 20
<212> TYPE: DNA
<213> ORGANISM: Artificial Sequence
<220> FEATURE:
<223> OTHER INFORMATION: TCR beta primers for individual V segments

<400> SEQUENCE: 215
ccaatttcag gccacaactc                                                 20

<210> SEQ ID NO 216
<211> LENGTH: 20
<212> TYPE: DNA
<213> ORGANISM: Artificial Sequence
<220> FEATURE:
<223> OTHER INFORMATION: TCR beta primers for individual V segments

<400> SEQUENCE: 216
ccaatttcag gacacgacta                                                 20

<210> SEQ ID NO 217
<211> LENGTH: 16
<212> TYPE: DNA
<213> ORGANISM: Artificial Sequence
<220> FEATURE:

```
<223> OTHER INFORMATION: TCR beta primers for individual V segments

<400> SEQUENCE: 217
tacttccgca accggg                                                       16

<210> SEQ ID NO 218
<211> LENGTH: 24
<212> TYPE: DNA
<213> ORGANISM: Artificial Sequence
<220> FEATURE:
<223> OTHER INFORMATION: TCR beta primers for individual V segments

<400> SEQUENCE: 218
ctcatttcgt tttatgaaaa gatg                                              24

<210> SEQ ID NO 219
<211> LENGTH: 23
<212> TYPE: DNA
<213> ORGANISM: Artificial Sequence
<220> FEATURE:
<223> OTHER INFORMATION: TCR beta primers for individual V segments

<400> SEQUENCE: 219
tgttacattt tgtgaaagag tct                                               23

<210> SEQ ID NO 220
<211> LENGTH: 21
<212> TYPE: DNA
<213> ORGANISM: Artificial Sequence
<220> FEATURE:
<223> OTHER INFORMATION: TCR beta primers for individual V segments

<400> SEQUENCE: 220
ccctgataac ttccaatcca g                                                 21

<210> SEQ ID NO 221
<211> LENGTH: 20
<212> TYPE: DNA
<213> ORGANISM: Artificial Sequence
<220> FEATURE:
<223> OTHER INFORMATION: TCR beta primers for individual V segments

<400> SEQUENCE: 221
aggtcctgaa aaacgagttc                                                   20

<210> SEQ ID NO 222
<211> LENGTH: 21
<212> TYPE: DNA
<213> ORGANISM: Artificial Sequence
<220> FEATURE:
<223> OTHER INFORMATION: TCR beta primers for individual V segments

<400> SEQUENCE: 222
ccttccagta ccaaaacatt g                                                 21

<210> SEQ ID NO 223
<211> LENGTH: 24
<212> TYPE: DNA
<213> ORGANISM: Artificial Sequence
<220> FEATURE:
<223> OTHER INFORMATION: TCR beta primers for individual V segments

<400> SEQUENCE: 223
aaggtctgaa attcatggtt tatc                                              24
```

```
<210> SEQ ID NO 224
<211> LENGTH: 23
<212> TYPE: DNA
<213> ORGANISM: Artificial Sequence
<220> FEATURE:
<223> OTHER INFORMATION: TCR beta primers for individual V segments

<400> SEQUENCE: 224
tgactttcag aaaggagata tag                                         23

<210> SEQ ID NO 225
<211> LENGTH: 16
<212> TYPE: DNA
<213> ORGANISM: Artificial Sequence
<220> FEATURE:
<223> OTHER INFORMATION: TCR beta primers for individual V segments

<400> SEQUENCE: 225
gggctccaag gccaca                                                 16

<210> SEQ ID NO 226
<211> LENGTH: 23
<212> TYPE: DNA
<213> ORGANISM: Artificial Sequence
<220> FEATURE:
<223> OTHER INFORMATION: TCR beta primers for individual V segments

<400> SEQUENCE: 226
agaaagcaga ataatcaat gag                                          23

<210> SEQ ID NO 227
<211> LENGTH: 24
<212> TYPE: DNA
<213> ORGANISM: Artificial Sequence
<220> FEATURE:
<223> OTHER INFORMATION: TCR beta primers for individual V segments

<400> SEQUENCE: 227
ttttgatttc ctttcagaat gaac                                        24

<210> SEQ ID NO 228
<211> LENGTH: 24
<212> TYPE: DNA
<213> ORGANISM: Artificial Sequence
<220> FEATURE:
<223> OTHER INFORMATION: TCR beta primers for individual V segments

<400> SEQUENCE: 228
ttgatctatt actcctttga tgtc                                        24

<210> SEQ ID NO 229
<211> LENGTH: 20
<212> TYPE: DNA
<213> ORGANISM: Artificial Sequence
<220> FEATURE:
<223> OTHER INFORMATION: TCR beta primers for individual V segments

<400> SEQUENCE: 229
gagatctttc ctctgagtca                                             20

<210> SEQ ID NO 230
<211> LENGTH: 16
<212> TYPE: DNA
<213> ORGANISM: Artificial Sequence
<220> FEATURE:
<223> OTHER INFORMATION: TCR beta primers for individual V segments
```

```
<400> SEQUENCE: 230
cacctggcac tgggag                                                    16

<210> SEQ ID NO 231
<211> LENGTH: 16
<212> TYPE: DNA
<213> ORGANISM: Artificial Sequence
<220> FEATURE:
<223> OTHER INFORMATION: TCR beta primers for individual V segments

<400> SEQUENCE: 231
ggctgggctt aaggca                                                    16

<210> SEQ ID NO 232
<211> LENGTH: 27
<212> TYPE: DNA
<213> ORGANISM: Artificial Sequence
<220> FEATURE:
<223> OTHER INFORMATION: TCR beta primers for individual V segments

<400> SEQUENCE: 232
atctatttct catatgatgt taaaatg                                        27

<210> SEQ ID NO 233
<211> LENGTH: 18
<212> TYPE: DNA
<213> ORGANISM: Artificial Sequence
<220> FEATURE:
<223> OTHER INFORMATION: TCR beta primers for individual V segments

<400> SEQUENCE: 233
tgacactgat cgcaactg                                                  18

<210> SEQ ID NO 234
<211> LENGTH: 15
<212> TYPE: DNA
<213> ORGANISM: Artificial Sequence
<220> FEATURE:
<223> OTHER INFORMATION: TCR beta primers for individual V segments

<400> SEQUENCE: 234
acaggctgca ggcag                                                     15

<210> SEQ ID NO 235
<211> LENGTH: 19
<212> TYPE: DNA
<213> ORGANISM: Artificial Sequence
<220> FEATURE:
<223> OTHER INFORMATION: TCR beta J segment specific primers

<400> SEQUENCE: 235
ttttccctgt gacggatct                                                 19

<210> SEQ ID NO 236
<211> LENGTH: 18
<212> TYPE: DNA
<213> ORGANISM: Artificial Sequence
<220> FEATURE:
<223> OTHER INFORMATION: TCR beta J segment specific primers

<400> SEQUENCE: 236
caggacagag tcctccct                                                  18

<210> SEQ ID NO 237
<211> LENGTH: 19
```

```
<212> TYPE: DNA
<213> ORGANISM: Artificial Sequence
<220> FEATURE:
<223> OTHER INFORMATION: TCR beta J segment specific primers

<400> SEQUENCE: 237 agccccttttt tgcaagttc                                              19

<210> SEQ ID NO 238
<211> LENGTH: 22
<212> TYPE: DNA
<213> ORGANISM: Artificial Sequence
<220> FEATURE:
<223> OTHER INFORMATION: TCR beta J segment specific primers

<400> SEQUENCE: 238
aactccgacc ttatgataca ct                                           22

<210> SEQ ID NO 239
<211> LENGTH: 19
<212> TYPE: DNA
<213> ORGANISM: Artificial Sequence
<220> FEATURE:
<223> OTHER INFORMATION: TCR beta J segment specific primers

<400> SEQUENCE: 239
tgccttcaag ggacaatgg                                               19

<210> SEQ ID NO 240
<211> LENGTH: 18
<212> TYPE: DNA
<213> ORGANISM: Artificial Sequence
<220> FEATURE:
<223> OTHER INFORMATION: TCR beta J segment specific primers

<400> SEQUENCE: 240
gatcattgca gtcaaacc                                                18

<210> SEQ ID NO 241
<211> LENGTH: 15
<212> TYPE: DNA
<213> ORGANISM: Artificial Sequence
<220> FEATURE:
<223> OTHER INFORMATION: TCR beta J segment specific primers

<400> SEQUENCE: 241
ggctgggctg ctcac                                                   15

<210> SEQ ID NO 242
<211> LENGTH: 15
<212> TYPE: DNA
<213> ORGANISM: Artificial Sequence
<220> FEATURE:
<223> OTHER INFORMATION: TCR beta J segment specific primers

<400> SEQUENCE: 242
atcccgccct ctcgg                                                   15

<210> SEQ ID NO 243
<211> LENGTH: 17
<212> TYPE: DNA
<213> ORGANISM: Artificial Sequence
<220> FEATURE:
<223> OTHER INFORMATION: TCR beta J segment specific primers

<400> SEQUENCE: 243
```

-continued

```
cagttccggg gcttcag                                                          17

<210> SEQ ID NO 244
<211> LENGTH: 16
<212> TYPE: DNA
<213> ORGANISM: Artificial Sequence
<220> FEATURE:
<223> OTHER INFORMATION: TCR beta J segment specific primers

<400> SEQUENCE: 244
gagcgcagtc tcgtcc                                                           16

<210> SEQ ID NO 245
<211> LENGTH: 18
<212> TYPE: DNA
<213> ORGANISM: Artificial Sequence
<220> FEATURE:
<223> OTHER INFORMATION: TCR beta J segment specific primers

<400> SEQUENCE: 245
cgcaaaaacc agacccaa                                                         18

<210> SEQ ID NO 246
<211> LENGTH: 16
<212> TYPE: DNA
<213> ORGANISM: Artificial Sequence
<220> FEATURE:
<223> OTHER INFORMATION: TCR beta J segment specific primers

<400> SEQUENCE: 246
ccgccttcca cctgaa                                                           16

<210> SEQ ID NO 247
<211> LENGTH: 15
<212> TYPE: DNA
<213> ORGANISM: Artificial Sequence
<220> FEATURE:
<223> OTHER INFORMATION: TCR beta J segment specific primers

<400> SEQUENCE: 247
gggaccgagg ggctg                                                            15
```